(12) United States Patent
Schiffrin et al.

(10) Patent No.: US 9,827,216 B2
(45) Date of Patent: Nov. 28, 2017

(54) NUTRITIONAL SUPPORT TO PREVENT AND/OR MITIGATE BONE MARROW TOXICITY FROM A CANCEROUS TUMOR

(75) Inventors: Eduardo Schiffrin, Crissier (CH); Kevin Burke Miller, Minneapolis, MN (US); Dominique Brassart, Chavannes-Pres-Renes (CH); Olivier Jacques Lantz, Paris (FR); Sebastian Diego Amigorena, Paris (FR)

(73) Assignees: Nestec S.A., Vevey (CH); Institut Curie, Paris (FR)

( * ) Notice: Subject to any disclaimer, the term of this patent is extended or adjusted under 35 U.S.C. 154(b) by 0 days.

(21) Appl. No.: 13/063,589

(22) PCT Filed: Sep. 11, 2009

(86) PCT No.: PCT/US2009/056599
§ 371 (c)(1),
(2), (4) Date: Jun. 1, 2011

(87) PCT Pub. No.: WO2010/033426
PCT Pub. Date: Mar. 25, 2010

(65) Prior Publication Data
US 2011/0223136 A1    Sep. 15, 2011

Related U.S. Application Data

(60) Provisional application No. 61/241,074, filed on Sep. 10, 2009, provisional application No. 61/098,258, filed on Sep. 19, 2008.

(51) Int. Cl.
| | |
|---|---|
| *A61K 31/20* | (2006.01) |
| *A61K 31/195* | (2006.01) |
| *A61K 31/7088* | (2006.01) |
| *A61K 35/747* | (2015.01) |
| *A61K 38/40* | (2006.01) |
| *A61K 38/01* | (2006.01) |
| *A61K 35/745* | (2015.01) |
| *A61K 38/17* | (2006.01) |
| *A61K 33/00* | (2006.01) |
| *A23L 33/00* | (2016.01) |
| *A23L 33/13* | (2016.01) |
| *A23L 33/135* | (2016.01) |
| *A23L 33/175* | (2016.01) |
| *A23L 33/19* | (2016.01) |

(52) U.S. Cl.
CPC ............ *A61K 31/195* (2013.01); *A23L 33/13* (2016.08); *A23L 33/135* (2016.08); *A23L 33/175* (2016.08); *A23L 33/19* (2016.08); *A23L 33/40* (2016.08); *A61K 31/20* (2013.01); *A61K 31/7088* (2013.01); *A61K 33/00* (2013.01); *A61K 35/745* (2013.01); *A61K 35/747* (2013.01); *A61K 38/018* (2013.01); *A61K 38/1783* (2013.01); *A61K 38/40* (2013.01); *A23V 2002/00* (2013.01)

(58) Field of Classification Search
None
See application file for complete search history.

(56) References Cited

U.S. PATENT DOCUMENTS

| 5,438,042 | A | * | 8/1995 | Schmidl et al. ............... 514/5.5 |
| 7,468,193 | B2 | | 12/2008 | Schiffrin et al. |
| 2003/0068385 | A1 | | 4/2003 | Moyer et al. |
| 2005/0090451 | A1 | * | 4/2005 | Klimberg et al. ............. 514/23 |

FOREIGN PATENT DOCUMENTS

| AU | 2009293476 | 3/2010 |
| WO | 96/34614 | 11/1996 |
| WO | WO 2005039318 A1 * | 5/2005 |

OTHER PUBLICATIONS

Daly et al. (Annals of Surgery, 221:327-338, 1995).*
http://www.impactinformation.com/home/index2.htm (accessed Aug. 9, 2013).*
Braga et al. (Arch. Surg., 137:174-180, 2002).*
Novartis (Novartis Impact Product detail, 2002; pp. 1-3).*
Bounous, "Whey Protein Concentrate (WPC) and Glutathione Modulation in Cancer Treatment," Anticancer Research, vol. 20, Nov. 2000, pp. 4785-4792.
Brittenden, et al., "L-arginine Stimulates Host Defenses in Patients with Breast Cancer," Surgery, vol. 115, No. 2, 1994, pp. 205-212.
Gentile, et al., "Approaches to Ablating the Myelotoxicity of Chemotherapy," Critical Review in Oncology/Hematology vol. 7, No. 1, Jan. 1987, pp. 71-87.
Guo, et al., "Chemoprotection Effect of Retroviral Vector Encoding Multidrug Resistance 1 Gene to Allow Intensified Chemotherapy in Vivo," Cancer Chemotherapy and Pharmacology, vol. 58, No. 1, Jul. 2006, pp. 40-49.

(Continued)

*Primary Examiner* — Brian Gangle
(74) *Attorney, Agent, or Firm* — K&L Gates LLP

(57) ABSTRACT

The present invention relates to methods and immunonutritional compositions for preventing or mitigating paralysis of the bone marrow, caused by a tumor or neoplasm, between cycles of and after anti-cancer therapy, thereby attaining a better efficacy of the treatment. More particularly, the present invention relates to methods and immunonutritional compositions that can transiently preventing or moderating, bone marrow paralysis or neutropenia of a subject tumor-induced apoptosis or necrosis or other cell damage such that the innate and adaptive immune functions and normal physiology of the bone marrow are preserved, at least in part, which, in turn, lead to (i) a better tolerance and increased efficacy to treatment; (ii) transient augmentation or enhancement of immunocompetence of the immune cell; and (iii) optimization of the effects of and increase of immunocompetence of the immune cell weakened due to paralysis of the bone marrow, caused by a tumor or neoplasm.

10 Claims, 11 Drawing Sheets

(56) References Cited

OTHER PUBLICATIONS

Heys, et al., "Potentiation of the Response to Chemotherapy in Patients with Breast Cancer by Dietary Supplementation with L-arginine: Results of a Randomised Controlled Trial," International Journal of Oncology, vol. 12, No. 1, Jan. 1998, pp. 221-225.

Kanwar, et al., "Iron-Saturated Lactoferrin is a Potent Natural Adjuvant for Augmenting Cancer Chemotherapy," Immunology and Cell Biology, vol. 86, No. 3, Mar. 2008, pp. 277-288.

Kennedy, et al., "The Use of a Whey Protein Concentrate in the Treatment of Patients with Metastatic Carcinoma: A Phase I-II Clinical Study," Anticancer Research, vol. 15, No. 6B, Nov. 1995, pp. 2643-2649.

de Moreno de Leblanc, et al., "Effects of Milk Fermented by *Lactobacillus helveticus* R389 on Immune Cells Associated to Mammary Glands in Normal and a Breast cancer Model," Immunobiology, vol. 210, No. 5, Sep. 2005, pp. 349-358.

Mego, et al., "Prevention of Febrile Neutropenia in Cancer Patients by Probiotic Strain *Enterococcus faecium* M-74. Phase II Study," Supportive Care in Cancer, vol. 14, No. 3, Mar. 2006, pp. 285-290.

Nomoto, et al., "Radioprotection of Mice by a Single Subcutaneous Injection of Heat-Killed *Lactobacillus casei* After Irradiation," Radiation Research, vol. 125, No. 3, Jan. 1991, pp. 293-297.

Nomoto et al., "Prevention of Indigenous Infection of Mice with *Escherichia coli* by Nonspecific Immunostimulation," Antimicrobial Agents and Chemotherapy, vol. 36, No. 2, Feb. 1992, pp. 361-367.

Osterlund, et al., "Lactobacillus Supplementation for Diarrhoea related to Chemotherpay of Colorectal Cancer: A Randomised Study," British Journal of Cancer, vol. 97, No. 8, Oct. 2007, pp. 1028-1034.

Roller, et al., "Consumption of Prebiotic Inulin Enriched with Oligofructose in Combination with the Probiotics *Lactobacillus rhamnosus* and *Bifidobacterium lactis* has Minor Effects on Selected Immune Parameters in Polypectomised and Colon Cancer Patients," British Journal of Nutrition, vol. 97, No. 4, Apr. 2007, pp. 676-684.

Scheid, et al., "Glutamine-Enriched Parenteral Nutrition Accelerates Nuetrophil Recovery After Chemotherapy for Acute Myeloid Leukemia," Blood, vol. 98, No. 11 Part 2, Nov. 2001, p. 221B.

Takagi, et al., "Enhancement of Natural Killer Cytotoxicity Delayed Murine Carcinogenesis by a Probiotic Microorganism," Carcinogenesis, vol. 22, No. 4, Apr. 2001, pp. 599-605.

Takahama, et al., "Adenovirus-Mediated Transfer of HST-1 (FGF-4) Gene Protects Mice from Lethal Irradiation," Proceedings of the Annual Meeting of the American Association for cancer Research, vol. 40, Mar. 1999, p. 5946.

Trumpler, et al., "Antibacterial Prophylaxis with Lactoferrin in Neutropenic Patients," European Journal of Clinical Microbiology & Infectious Diseases, vol. 8, No. 4, Apr. 1989, pp. 310-313.

M. Mego, et al., "Prevention of febrile neutropenia in cancer patients by probiotic strain *Enterococcus faecium* M-74. Phase II study," Support Care Cancer, 2006, vol. 14, pp. 285-290.

Nakamura et al. "Influence of preoperative administration of ω-3 fatty acid-enriched supplement on inflammatory immune responses in patients undergoing major surgery for cancer" Nutrition, vol. 21, 2005, pp. 639-649.

Takeuchi et al. "Clinical Significance of Perioperative Immunonutrition for Patients with Esophageal Cancer" World J. Surg., vol. 31, 2007, pp. 2160-2167.

Brittenden et al. "Natural cytotoxicity in breast cancer patients receiving neoadjuvant chemotherapy: effects of L-arginine supplementation" European Journal of Surgical Oncology, vol. 20, 1994, pp. 467-472.

\* cited by examiner

NUTRITIONAL SUPPORT TO PREVENT AND/OR MITIGATE BONE MARROW TOXICITY FROM A CANCEROUS TUMOR

CROSS REFERENCE TO RELATED APPLICATIONS

The present application is a National Stage of International Application No. PCT/US009/56599, filed on Sep. 11, 2009, which claims priority to U.S. Provisional Application No. 61/241,074, filed on Sep. 10, 2009, which claims priority to U.S. Provisional 61/098,258, filed on Sep. 19, 2008, the entire contents of each of which are being incorporated herein by reference.

TECHNICAL FIELD

The present invention relates to methods and an immuno-nutritional compositions for preventing and/or mitigating bone marrow toxicity caused by a tumor or neoplasm.

BACKGROUND

Apoptosis is a type of program cell death mechanism occurring in multi-cellular organisms that promotes cellular homeostasis by eliminating unnecessary or malfunctioning cells. Abnormalities in the apoptotic mechanism can contribute to tumorigenesis, e.g., escape of the tumor cells from the apoptotic signals, as well as resistance to anti-cancer therapies, such as, radiation therapy and chemotherapy.

Tumor cells evade the innate and adaptive immune responses (immunosurveillance) by immunoselection (selection of non-immunogenic tumor cell variants or also known as immunoediting in the mouse model) or immunosubversion (active suppression of the immune response). Zitvogel, L., J. Clin. Invest., 118:1991-2001, 2008; Koebel, C. M., Nature, 450:903-907, 2007; Zitvogel, L. et al., Nat. Rev. Immunol., 6:715-727, 2006. However, tumor cells can escape the immune control through other mechanisms involving tumor-derived factors, which may interfere with the anti-tumor immune response.

Chronic and smoldering inflammation increases the risk of neoplasia. Infectious agents are estimated to be involved in over 15% of the malignancies worldwide. Balkwill, F. et al., Cancer Cell, 7:211-217, 2005. An inflamed tissue environment can promote the development of cancer cells and immunosuppression might be a necessary component to counteract the "immunosurveillance" that protects the host against tumor development (Koebel, C. M. et al., supra). In addition, once the tumors developed, they can sustain an inflammatory state and recruit pro-inflammatory and immunosuppresive myeloid derived cells such as monocytes. An accumulation of cells from the bone marrow and other immune compartments of myeloid cells of cancer patients called "myeloid suppressor cells (MSC)" is associated with a suppressor activity on T cell activation (Galina, G. et al., J. Clin. Invest., 116:2777-2790, 2006).

As discussed above, the anti-tumoral defense, i.e., the immune system, is usually impaired in its capacity to control the presence and overgrowth of transformed tumoral cells. In addition, it also suffers from further functional impairment due to the toxicity of anti-cancer therapies.

The success of anti-cancer therapies such as radiotherapy and chemotherapy rely not only on their cytotoxic effects on the tumor cells but also on the concurrent immunocompetence during treatment. The necessary robustness of the immune function during anti-cancer treatment involves both the innate and the adaptive immune responses working in concert with anti-cancer drugs or radiotherapy. Apetoh, L. et al., Nature Med., 13:1050-1059, 2007.

Recent studies have revealed that tumor cells undergoing chemo- or radiotherapy-induced apoptosis are able to induce a potent immune response due to an increase in transient immunogenic activity. By inducing immunogenic determinants, tumor cells can transiently express "danger signals" on their cell surfaces that promote their phagocytosis by dendritic cells (DC), induce DC maturation and stimulation of the immune response. Examples of immunogenic determinants induced on dying tumor cells, include but are not limited to, heat shock proteins (HSP70 and HSP90), ligands for natural killer receptors (e.g., NKG2D), high mobility group box 1 protein (HMGB1), all of which are "danger signals" that activate the immune system. For example, HMGB1 can activate immune cells through reaction with TL4R (TLR-4). There are other danger signals, however, that fail to enhance an immune response. For example, calreticulin, which is expressed on the tumor cell surface upon induction of cell death upon anti-cancer treatment, can promote phagocytosis by DC. DC signaling by calreticulin, however, is insufficient to activate an anti-tumor immune response. Additional signaling pathways triggered by ligands of Toll-like receptors (TLRs) (probably also by other receptors) are required. Gardai, S. J. et al., Cell, 123:321-334, 2005.

The Toll-like receptors (TLRs) play a key role in the regulation of the immune system. They have the ability to recognize microbes and directly initiates specific signal transduction pathways that alert the host defenses. TLR ligands involve both non-self bacterial motifs and endogenous "danger signals." An example of an endogenous danger signals is the high-mobility-group box 1 (HMGB1) protein, upon reaction with TLR4, is able to activate DC and generate an immune response against dying tumor cells and complement the efficacy of anti-cancer treatment, i.e., chemo- and radiotherapy (Apetoh, L. et al., Nature Med., 13:1050-1059, 2007). Because HMGB1 is released from irradiated tumor cells some hours after irradiation, it seems to be one of the major "danger signal" contributing to the immunogenicity of dying tumor cells.

Other ligands of TLR4 with the potential capacity to induce cell activation are hyaluronans (extracellular matrix), heat shock proteins (HSP), and fibronectin. HSP 70 and HSP 90 are major determinants to the immunogenicity of stressed dying cells (Tesniere, A. et al., Cell Death & Differentiation, 15:3-12, 2008).

Other danger signals released from apoptotic/necrotic cells such as uric acid, RNA, DNA, potassium (K), nucleotides are able to activate the innate immune response and thereafter an adaptive immune response.

DNA damage causes cells to upregulate expression of ligands for the NKG2D receptors expressed on NK cells and activated CD8 T cells and that can result in a cytotoxic response (Gasser, S. et al., Cancer Res., 66:3959-3962, 2006). Tumor cells tend to down regulate NKG2D ligands and thereby escape immune detection. However, during genotoxic-stress induction by anti-cancer treatment, cancerous cells upregulate NKG2D ligands and become a "visible" target for cytotoxic NK or CD8 lymphocytes.

Other danger signals expressed or released by stressed cancer cells can bind to a group of cytosolic proteins called NODs/NACHT-LRHs (NLRs) or inflammasome that activate the caspase-1 and thereby contribute to the release of pro-inflammatory cytokines such as IL-1 j and IL-18 (Martinon, F., Trends in Immunol., 26(8):447-454, 2005).

In addition, it has been reported that combination of danger signals such as HMGB1 with DNA (CpG) can induce production of interferon-α signaling through TLR4 and TLR9 (Ivanov, S. et al., Blood, 110:1970-1981, 2007).

Many of the above-mentioned molecules that represent "danger signals" can be released from tumor cells and tissues as a consequence of the anti-cancer treatment in contrast to the silent growth of tumors during long periods of time. As a consequence of tumor cell death induction by anti-cancer treatment, these tumor cells become transiently more immunogenic. However, such transient increase in immunogenicity of the tumor cells is not advantageous to the host, if at the same time, the immune cell function is suffering from the toxicity induced by anti-cancer treatments. This is because anti-cancer therapies also frequently induce myelosuppression and/or thymolysis, which, in turn, cause the immune system to miss the transient increase of antigenicity and immune stimulatory capacity of dying tumor cells during treatment. Moreover, anti-cancer therapies target tumor cells, actively dividing lymphocytes and innate immune cells, all of which are needed to mount an immune response. To overcome this dilemma, immunotherapy has been proposed to counteract the transient immunosuppression induced by anti-cancer therapies. For this very reason, anti-cancer therapies and immunotherapy have been perceived as antagonistic. van der Most, R. G. et al., Cell Death Differentiation, 15:13-20, 2008. Unfortunately, immunotherapy alone is not sufficient to protect the non-tumor dividing cells from the cytotoxic effects of anti-cancer therapy. Many types of toxicities are induced by the anti-cancer treatments on the different cell subsets of the immune system such as apoptosis, autophagy and impaired capacity of activation. Because the immune cells suffer from the side effects of anti-cancer therapy, the opportunity to profit from this window of increased immunogenicity is greatly reduced. In the process of experiencing the side effects of cancer therapy-induced apoptosis, antigen-presenting cell function, innate cell killing and antigen specific tumor cell killing are also affected in the host. The period of transient enhancement of immunogenicity in cancer-therapy-induced cell death represents an opportunity for the immune system to recover the control on the transformed cells and keep in check the remaining viable tumor cells. To profit from this window of enhanced antigenic or immunogenic expression, the present invention provides methods and immunonutritional compositions, which when applied and administered to a patient undergoing stress-induced apoptotic cancer therapy, would further enhance their innate immune response and anti-tumor immune response. Therefore, by nutritional conditioning of the immune system (via immunonutrition) around the cycles of chemo- and radiotherapy treatment, acute immune toxicity induced by such treatment can be corrected and which, at the same time, corresponds paradoxically to a moment of enhanced immunogenicity of the tumor cells.

Tumor cells undergoing the cellular stress and expressing "danger signals" and death induced by the anti-cancer treatment can become a more "visible" target to the innate response against and thereby be more easily attacked by innate effector cells, such as natural killer (NK) cells, natural killer T (NKT) cells, gamma-delta (γδ) T cells and killer dendritic cells (KDC). Pillarisetty, V. G. et al., J. Immunol., 174:2612-2618, 2005. In addition, activated DC can stimulate a tumor antigen-specific cytolytic T cell response. Activation of the innate immune responses can be enhanced by administering exogenous agents or adjuvants, ligands for co-stimulatory proteins, cytokines, or drugs. For example, nucleic acid recognition (e.g., double stranded RNA, nucleotides) by DC through endosomal located TLRs (TLR3, TLR9) can help the DC activation and subsequently an antigen-specific anti-tumor immune response. Blattman, J. N. et al., Science, 305:200-205, 2004. Another example, CpG, an oligonucleotide, can enhance the capacity to attain the NK-like activity by DC and can increase the status of DC activation and prevent thereby the "tolerogenic" signals generated by the tumor and the conditioned immune cells by the tumor like alternatively activated macrophages.

There are many other nutrients that have shown activities to increase innate immune function (immunonutrients). For example, some non-pathogenic probiotic bacteria have the capacity to activate macrophages, dendritic cells and natural killer (NK) cells which would lead to the improvement of antigen presentation and innate destruction of tumor cells. As mentioned above, nucleotides, acting as surrogate signal of danger, can activate the immune system. Stimulation of immune reactivity by DNA, RNA and CpG has been confirmed by several studies.

Arginine and citrulline, as well as branched-chain amino acids, can stimulate protein synthesis through mTOR signaling, which, in turn, prevents the autophagic process on immune cells that may be induced by the stress of anti-cancer treatments. Glutamine can increase the innate cytolytic activity of NK, macrophages and killer dendritic cells can contribute to the antigen-specific cytolytic activity of $CD8^+$ T cells against tumor cells. Some bacterial or yeast molecular patterns can stimulate the activity of innate lymphocyte populations, e.g., NK, NKT and gamma-delta T cells, with cytotoxic activities against tumor cells and promote enhanced activation of the antigen-presenting cells to process and present tumor antigens to $CD4^+$ and $CD8^+$ T cells.

Several nutrition formulas supplemented with one or more of these immunonutrients having immune-modulating properties, have been developed.

U.S. Pat. No. 6,210,700 generally describes an improved immunomodulatory therapy for enhancement of depressed host defense mechanisms and improving allograft survival rates which includes the use of omega-9 unsaturated fatty acids to alter the immune response associated with organ transplantation It is administered, optionally, in conjunction with an immunomodulatory diet comprising arginine and its salts, or metabolic precursors of arginine, together with an immuno-suppressive treatment comprising the administration of cyclosporine or other immuno-suppressants and optionally, with or without a donor specific transfusion. An especially preferred source of the omega-9 unsaturated fatty acids is canola oil.

U.S. Pat. No. 5,330,972 generally describes that apoptosis of CD4 cells in a person infected with the human immunodeficiency virus may be impeded by enterally feeding to the infected person with a nutritional product that contains soy protein hydrolysate having a degree of hydrolysis in the range of about 14 to 17, and a molecular weight partition, as determined by size exclusion chromatography, wherein 30%-60% of the particles have a molecular weight in the range of 1500-5000 daltons. The nutritional product also contains a source of intact protein and dietary fiber. The nutritional product has a ratio, by weight, of n-6 to n-3 fatty acids of about 1.3:1 to 2.5:1.

U.S. Pat. No. 5,576,351 relates to the treatment of an impaired human immune response or to reduction of the severity of degradation of the human immune response by the administration of arginine or ornithine, or a functional analog of arginine or ornithine, or mixtures thereof, to humans suffering from an impaired immune response or at risk of suffering an impaired immune response. Such treatment is provided by enterally administering compositions supplemented with arginine or ornithine, or functional analogs of arginine or ornithine, or parenterally administering amino acid solutions supplemented with arginine or ornithine, or functional analogs of arginine or ornithine, to the patient.

U.S. Patent Application Publication No. 2008/0231525 describes a nutrient composition that is parenterally delivered to a critically ill patient or for the purpose of improving mitochondrial function. The nutrient composition includes a combination of a glutamine precursor molecule and an anti-oxidant, e.g., selenium, vitamin C, zinc, vitamin E, and beta-carotene.

U.S. Patent Application Publication No. 2005/0090451 generally describes a method of protecting non-mucosal tissue against damage from radiation therapy via the administration of a composition that includes a therapeutically effective amount of glutamine or a pharmaceutically acceptable salt.

U.S. Patent Application Publication No. 2005/0238660 A1 relates to methods and compositions of an immunostimulatory nucleic acid in combination with other therapeutic formulations such as oil-in-water emulsions. The combination of therapeutics is administered to non-human subjects in various dosages or at various time schedules for the treatment of disorders such as disease and cancer.

However, none of the prior art cited, as discussed herein, describes or suggests the addition of the immunonutrients to cancer patients undergoing cancer therapy-induced apoptosis and/or necrosis, at a time when the dying tumor cells are undergoing the window of enhanced antigenic or immunogenetic expression. After all, the goal of immunonutrition should be to counter balance tumor-induced immune tolerance during anti-cancer therapy-induced cell death or damage, thereby tipping the balance of host-tumor balance towards the reinforcement of the host defenses. At the same time, immunonutrition, when provided to cancer patients, can enhance antigen-presenting cell function and innate cell destruction of the transformed cells and antigen-specific tumor cell destruction. In the end, the major target of immunonutrition, as proposed herein, should be on the non-tumoral cells that are transiently weakened by anti-cancer therapy treatment.

Based on the above, there is a need for methods and immunonutritional compositions that can be formulated for preventing the impairment of the immune function of cancer patients during the anti-cancer treatment to attain a better efficacy of treatments. There is also a need for methods and immunonutritional compositions, which when applied and administered in combination with anti-cancer therapies would produce less adverse side effects to cancer patients. More importantly, there is a long felt need for methods and immunonutritional compositions that can be employed at the time when dying tumor cells undergo a window of immunogenicity, which act in concert with the prescribed anti-cancer therapy and further enhance innate and adaptive immune processes of the host to enhance tumor cell killing. There is also an urgent need for methods and immunonutritional compositions that can preserve the normal physiology of the immune cells and other hemopoeitic cells (i.e. bone marrow) and rescue their immunocompetence that were damaged by anti-cancer therapy.

The methods and compositions and the means of accomplishing each of the above needs, as well as others, will become apparent from the detailed description which follows thereafter.

SUMMARY

The present invention provides methods and immunonutritional compositions for preventing the impairment of immune function of cancer patients undergoing anti-cancer therapy to obtain a better efficacy of such treatment, and minimize undesirable side effects of the treatment and thus allow a patient to maintain therapy (compliance with treatment) and have an improved quality of life.

To this end, the present invention provides a method for transiently augmenting or enhancing immunocompetence of an immune cell of a subject undergoing anti-cancer therapy-induced apoptosis and tumor-cell-enhanced immunogenicity, which includes exposing the immune cell to an immunonutritional composition that includes at least one immuno-enhancing agent capable of preserving the innate and adaptive immune functions and normal physiology of the immune cell. The preservation of the immune functions result in an increased efficacy of the anti-cancer therapy and transient augmentation or enhancement of immunocompetence of the immune cell.

In one embodiment, the present invention also provides a method of transiently augmenting or enhancing the immunogenecity of a tumor cell of a subject undergoing anti-cancer therapy-induced apoptosis, which involves exposing the tumor cell of the subject to an immunonutritional composition that contains at least one immuno-enhancing agent capable of inducing at least one immunogenic determinant in the tumor cell. The induction of at least one immunogenic determinant results in a transient augmentation or enhancement of immunogenecity of the tumor cell.

In another embodiment, the present invention further provides a method of transiently augmenting or enhancing the immunocompetence of an immune cell and the immunogenecity of a tumor cell of a subject undergoing anti-cancer therapy-induced apoptosis, which comprises exposing the immune cell and tumor cell of a subject to an immunonutritional composition, which comprises at least one immuno-enhancing agent that is capable of (1) preserving the innate and adaptive immune functions and normal physiology of the immune cell and (2) inducing at least one immunogenic determinant in the tumor cell. The preservation of the immune functions and normal physiology of the immune cell results in a better tolerance and increased efficacy of the anti-cancer therapy and transient augmentation or enhancement of immunocompetence of the immune cell. Similarly, the induction of at least one immunogenic determinant results in a transient augmentation or enhancement of immunogenecity of the tumor cell.

In one embodiment, the immuno-enhancing agent, according to the present invention, is capable of (1) optimizing the effects of and increasing the immunocompetence of the immune cell weakened by anti-cancer therapy and (2) inducing at least one immunogenic determinant of both the immune cell and tumor cell.

In another embodiment of the present invention, the immunonutritional compositions can be administered to the patient from between ten and three days before one cycle of anti-cancer therapy to between ten and seven days after the cycle.

In another embodiment of the present invention, the immunonutritional compositions can be administered to the patient from between ten and three days before one cycle of anti-cancer therapy to between ten and seven days after the surgical removal of all or part of the tumor.

In another embodiment of the present invention, the immunonutritional compositions can be administered to the patient from between ten and three days before one cycle of anti-cancer therapy to between ten and just prior to the surgical removal of all or part of the tumor.

In another embodiment, at least one immuno-enhancing agent may be a probiotic, a probiotic biomass, a non-replicating organisms, a protein source, a fatty acid, an amino acid, a nucleic acid, potassium, uric acid, a single-stranded oligonucleotide, a pathogen/microbial associated molecular pattern (PAMP/MAMP), an active hexose correlated compound, carotenoids, vitamin D (including vitamin D precursors, active forms, agonists or synthetic analogs of vitamin D, and their various states of hydroxylation (25-OH D or 1,25-OH D)). a vitamin D receptor, branched-chain amino acids, theanine, vitamin E, essential fatty acids such as EPA and DHA or EPA/DHA, and Lactoferrin protein, including any state of iron-enrichment (e.g., apo-lactoferrin, holo-lactoferrin, and iron-saturated Lactoferrin)

In yet another embodiment, the probiotic can be a microorganism such as *Bifidobacterium lactis, Bifidobacterium longum, Lactobacillus paracasei, Lactobacillus johnsonii Lactobacillus reuterii* or mixtures thereof. The protein source can be whey, casein or soy protein. The whey protein source is derived from native whey, intact unhydrolyzed whey, whey protein concentrate, whey protein isolate or whey protein hydrolysate. Casein and soy proteins may be in form of casein and soy protein hydrolysates.

In an additional embodiment of the present invention, the immuno-enhancing agent can be at least one amino acid, e.g., a branched chain amino acid such as leucine, isoleucine, and valine; glutamine, arginine, citrulline, cysteine and threonine. The immuno-enhancing agent can be a ribonucleic acid (RNA), a deoxyribonucleic acid (DNA) or at least one oligodeoxynucleotide, e.g., a CpG oligodeoxynucleotide.

In one embodiment of the present invention, at least one immunogenic determinant is selected from the group consisting of heat shock protein 70 (hsp70), heat shock protein 90 (hsp90), natural killer cell receptor ligands (e.g., NKG2D ligands), calreticulin, and high mobility group box 1 protein (HMGB1).

An advantage of the present invention is to preserve the cell viability and the activation capacity of antigen presenting cells, other innate immune cells, NK, NKT, γδT and KDC during the transient augmentation of immunogenicity of the apoptotic tumor cells due to the treatment effect.

In one specific embodiment of the present invention, the transient preservation of the immunocompetence of antigen presenting cells and innate cytotoxic cells during the augmentation of tumor cell immunogenicity of the subject occurs from between ten and three days before one cycle of anti-cancer therapy to between ten and seven days after the cycle. In another embodiment, the antigen-presenting cell and cytotoxic cells can be a macrophage, dendritic cell, a killer dendritic cell, or a natural killer cell (e.g., NK, NKT) and a cytotoxic $CD8^+$ T cell (CTL).

The present invention also provides immunonutritional compositions that include at least one immuno-enhancing agent as used by the methods as described above and herein below.

It is contemplated that any method or composition described herein can be implemented with respect to any other method or composition described herein. Moreover, it is clearly contemplated that embodiments may be combined with one another, to the extent that they are compatible.

Other features and advantages of the present invention are apparent in the detailed description that follows. It should be understood, however, that the detailed description and the specific examples, while indicating embodiments of the present invention, are given by way of illustration only, not limitation. Various changes and modifications within the scope of the invention will become apparent to those skilled in the art from the detailed description.

DETAILED DESCRIPTION

Figure 1:
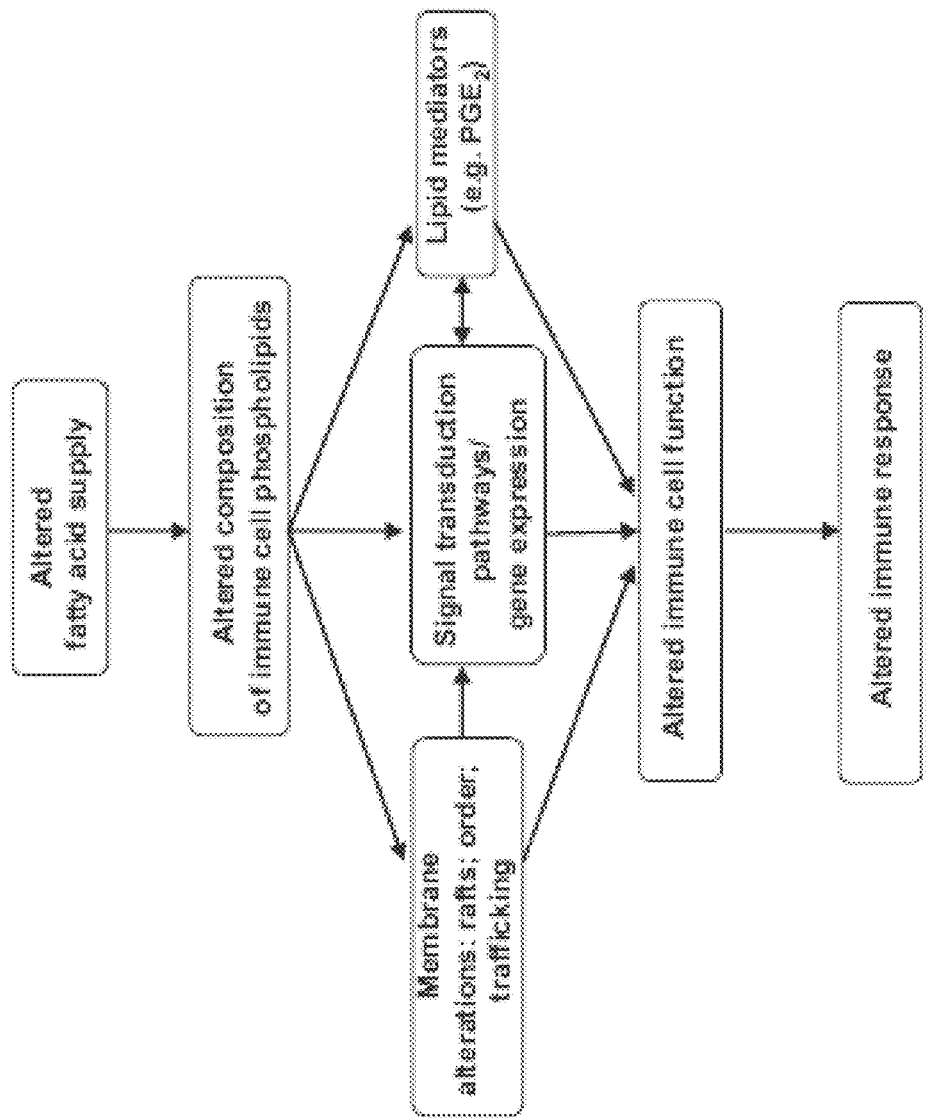
FIG. 1 illustrates ways in which changes in membrane phospholipid fatty acid composition may influence immune cell function in accordance with an embodiment of the present disclosure.

Before the present methods and compositions are described, it is to be understood that this invention is not limited to particular methods, compositions, and experimental conditions described, as such methods and compounds may vary. It is also to be understood that the terminology used herein is for the purpose of describing particular embodiments only, and is not intended to be limiting, since the scope of the present invention will be limited only to the appended claims. All publications mentioned herein are incorporated herein by reference in their entirety to disclose and describe the methods and/or materials in connection with which the publications are cited.

Prior to setting forth the present invention, the following terms are defined to provide a better understanding of the present invention.

As used herein, the terms "cancer" and "tumor" are used interchangeably herein and refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

As used herein, animals include, but is not limited to mammals which includes but is not limited to rodents, aquatic mammals, domestic animals such as dogs and cats, farm animals such as sheep, pigs, cows and horses, and humans. Wherein the terms animal or mammal or their plurals are used, it is contemplated that it also applies to any animals that are capable of the effect exhibited or intended to be exhibited by the context of the passage.

As used herein, "bone marrow paralysis" is meant to include suppression or cessation of bone marrow activities, including but not limited to bone marrow's role in immune functions and hemopoiesis.

As used herein, "complete nutrition" are preferably nutritional products that contain sufficient types and levels of macronutrients (protein, fats and carbohydrates) and micronutrients to be sufficient to be a sole source of nutrition for the animal to which it is being administered to.

As used herein, "incomplete nutrition" are preferably nutritional products that do not contain sufficient levels of macronutrients (protein, fats and carbohydrates) or micronutrients to be sufficient to be a sole source of nutrition for the animal to which it is being administered to.

As used herein, "Long term administrations" are preferably continuous administrations for more than 6 weeks.

As used herein "microorganism" is meant to include the bacterium, yeast and/or fungi, a cell growth medium with the microorganism or a cell growth medium in which microorganism was cultivated.

As used herein, a "Prebiotic" is preferably a food substances that selectively promote the growth of beneficial bacteria or inhibit the growth of pathogenic bacteria in the intestines. They are not inactivated in the stomach and/or upper intestine or absorbed in the GI tract of the person ingesting them, but they are fermented by the gastrointestinal microflora and/or by probiotics. Prebiotics are, for example, defined by Glenn R. Gibson and Marcel B. Roberfroid, Dietary Modulation of the Human Colonic Microbiota: Introducing the Concept of Prebiotics, J. Nutr. 1995 125: 1401-1412.

As used herein, Probiotics micro-organisms (hereinafter "probiotics") are preferably microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. (Salminen S, Ouwehand A. Benno Y. et al "Probiotics: how should they be defined" Trends Food Sci. Technol. 1999:10 107-10). In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products.

As used herein, "Short term administrations" are preferably continuous administrations for less than 6 weeks.

As used herein, a "tube feed" is preferably a complete or incomplete nutritional products that are administered to an animal's gastrointestinal system, other than through oral administration, including but not limited to a nasogastric tube, orogastric tube, gastric tube, jejunostomy tube (J-tube), percutaneous endoscopic gastrostomy (PEG), port, such as a chest wall port that provides access to the stomach, jejunum and other suitable access ports.

All dosage ranges contained within this application are intended to include all numbers, whole or fractions, contained within said range.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject. A "subject" can also refer to a cancer patient who is undergoing anti-cancer therapy-induced apoptosis, either during or after anti-cancer treatment.

As used herein, the terms "treatment", "treat" and "to alleviate" is preferably to both prophylactic or preventive treatment (that prevent and/or slow the development of a targeted pathologic condition or disorder) and curative, theraputic or disease-modifying treatment, including therapeutic measures that cure, slow down, lessen symptoms of, and/or halt progression of a diagnosed pathologic condition or disorder, and treatment of patients at risk of contracting a disease or suspected to have contracted a disease, as well as patients who are ill or have been diagnosed as suffering from a disease or medical condition. The terms "treatment", "treat" and "to alleviate" also refer to the maintenance and/or promotion of health in an individual not suffering from a disease but who may be susceptible to the development of an unhealthy condition, such as nitrogen imbalance or muscle loss. The terms "treatment", "treat" and "to alleviate" are also intended to include the potentiation or otherwise enhancement of one or more primary prophylactic or therapeutic measure.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

It is specifically contemplated that any embodiments described in the Examples section are included as an embodiment of the invention.

The terms "a" and "an," when used in conjunction with the word "comprising" in the claims or specification, denotes one or more, unless specifically noted.

Immunonutritional agents or immunonutrients are dietary components that provide specific effects on the immune system of or can confer additive benefits to patients undergoing the adverse effects of starvation, illness or surgery and anti-cancer therapy-induced apoptosis. These agents, known to stimulate the immune function when administered enterally or parenterally to the patients, are found to be potentially effective in improving the outcome during pre-operative or pre-cancer-therapy treatment period and reducing the opportunity for post-operative infections and lessening hospital stay. Examples of commercially-available enteral immunonutritional regimens having immune-enhancing effects include Impact® (Novartis Nutrition, Minneapolis) and Immune-Aid@ (McGaw, Inc, Irvine Calif.), Immunex-Plex® (Victus, Inc., Miami, Fla.) and AlitraQ® (Ross laboratories, Columbus Ohio). These regimens contain key nutrients such as glutamine, w-3 fatty acids, arginine and/or ribonucleic acid but in differing compositions and quantities in different formulation are commercially available. The effects of these key nutrients are summarized in Table 1 of Heys, S. D. et al., Nutr. Hosp. 19:325-332, 2004. The immunonutrients can be added to standard nutritional formulations for patients who had undergone cancer surgery, e.g., gastrointestinal cancer surgery and pancreatic cancer surgery or anti-cancer therapy or are in the process to undergo such surgery or treatment. Braga, M. et al., Nutritional Therapy & Metabolism, 24:115-119, 2006; McCowen, K. C. et al., Am. J. Clin. Nutr. 77:764-770, 2003; Slotwiiski, R. et al., Centr. Eur. J. Immunol., 32(3):147-154, 2007. They are preferably administered to cancer patients as an enteral formulation. They can be given pre-, peri- and post-operatively or during pre-, peri- and post-anti-cancer therapy treatment. Studies have indicated, however, that pre-operative and peri-operative supplementations of immunonutrients are more effective in improving the clinical outcome of GI cancer patients than post-operative treatment. When immunonutrition was given post-operatively, the results were conflicting, probably because the amount of substrates given to cancer patients in the first five days after surgery was insufficient to reach adequate tissue and plasma concentration quickly enough to be active. In fact, it takes about 5 days for the immunonutrients to be incorporated into the host tissues and, hence, modulate inflammatory mediators and fatty acid profiles. Braga, M. et al. supra; McCowen, K. C. et al., supra. To date, however, questions pertaining to the immunomodulatory effects of enteral immunonutrition on a cancer patient, either administered during the pre-, peri- or post-operative period, remains yet to be answered.

The term "immuno-enhancing agent" or "immunonutritional" involves the administration of specific nutritional compounds that have "immuno-enhancing," "immuno-potentiating" or "immuno-augmenting" qualities to the overall immune system of the patients undergoing cancer therapy or anti-tumoral therapy or patients with impaired immune function with the purpose of altering tumor-induced cytotoxic effects, improving clinical outcome and further preserving and enhancing innate and adaptive immune processes of the immune host to activate tumor cell killing in response to the induction of the immunogenic determinants, as exemplified above. Examples of immuno-enhancing nutritional compounds include amino acids such as L-arginine, citrulline, cysteine, glutamine, threonine, omega-3 fatty acids and nucleotides. Other examples of immuno-enhancing agents include a probiotic, a probiotic biomass, a non-replicating organisms, a protein source, a fatty acid, an amino acid, a nucleic acid, potassium, uric acid, a single-stranded oligonucleotide, a pathogen/microbial associated molecular pattern (PAMP/MAMP), an active hexose correlated compound, carotenoids, a vitamin D receptor, branched-chain amino acids, theanine, vitamin E, essential fatty acids such as EPA and DHA or EPA/DHA.

Immuno-enhancing nutritional compositions may be administered via intergastric feeding.

As used herein, the term "peri-operative period" refers to the time period surrounding a patient's surgical procedure; this commonly includes ward admission, anesthesia, surgery, and recovery. Peri-operative generally refers to the three phases of surgery: preoperative, intraoperative, and postoperative. The goal of perioperative care is to provide better conditions for patients before operation, during operation, and after operation, including neoadjuvant treatment. Similarly, pre-, peri-, and post-anti-cancer therapy treatment refers to the period before, during and after cancer chemotherapy or radiotherapy.

As used herein, the term "Neoadjuvant" or "Neoadjuvant Treatment" refers to a treatment in an effort to make a neoplasm/tumor more amicable to a more aggressive treatment, such as centralizing the tumor (shrinking projects) and/or shrinking the tumor, and reducing the risk of cancer cell seeding during surgical removal.

As used herein, the term "aggressive treatment" is intended to refer to surgical treatments, including traditional surgery and radio-tactic surgery, chemotherapeutic treatments, hormonal treatments and radiotherapeutic treatments.

The mechanism of cell death according to the present invention is via chemotherapy- or radiotherapy-induced cell death or apoptosis. The apoptosis cell death induced by such treatments will be an immunogenic cell death because all of the tumor cells are exposed to cellular stress prior to death.

Transient increase of antigenecity or immunogenicity applies to the tumoral cells undergoing anti-cancer therapy-induced cell death. The impact and target of the immunonutritional compositions, according to the present invention, act more preferably on the overall immune cells of the subject to preserve their immunocompetence during the stress of treatment, it cannot been excluded though that nutrients such as glutamine could enhance the expression of HSP on the stressed tumoral cells and thereby increase even more of their immunogenicity. In general, apoptosis is a type of cell death that is not efficient to trigger innate adaptive immune response. In some cases, however, apoptotic cell death can convey with the expression of "danger signals" and thereby have a stimulatory capacity of the immune system. In addition, immune response potentially generated during this specific moment can counter balance the tolerogenic response that tumor induce in their own benefit to escape the immune response.

Thus, one strategy that is used in immunotherapy is to prevent the immune tolerance that can be triggered by tumor antigen processing and presentation by non-activated antigen presenting cells, e.g., dendritic cells. Some studies have shown that if tumor agonists such as the CpG oligodeoxynucleotides (ODNs), and other nucleotides, RNA, DNA, and other danger signals, the anti-cancer immune reaction can be better stimulated.

CpG ODNs stimulate cells that express Toll-like receptor 9, which initiates an immunomodulatory cascade that result in the activation of B and T lymphocytes, natural killer cells, monocytes, macrophages, and dendritic cells. CpG ODNs improve the host ability to resist infection by accelerating and improving the induction of the innate and adaptive immune responses. Klinman, D. M. et al., Expert Opin. Biol. Ther., 4(6):937-946, 2004.

In addition, dendritic cells (DC) may exert more primitive innate immune cell function, i.e., the ability to kill transformed (cancer) cells. This function has been ascribed to a type of dendritic cell referred by others as killer dendritic cell (KDC). KDC has the ability to kill tumoral cells through a diversity of mechanisms that prevent escape of "resistant" tumor cells to a single mechanism of death.

The dysfunction of the double DC function during treatment, namely, antigen presentation and tumor cell killing, can be prevented by the activation of DC population through the immuno-nutritive interventions. The combined approach of anti-cancer treatment such as chemotherapy and/or radiotherapy with immuno nutrition can preserve immune competence which would provide a potential benefit to makes the cycles more efficient, improve tolerance to the immune toxicity of the treatments that can lead to mucosal damage (mucositis) and a higher incidence of infections.

Natural killer cells and natural killer T cells are also involved in innate cell killing of the tumor cells. Their functional capacity is highly impaired during anti-cancer treatment. To accomplish this function, however, these cells need to remain capable of being activated and to go through cell cycle to expand their cell population.

Selected probiotics and other microbial associated molecular patterns (MAMPs) have the capacity to stimulate this cell population and thereby exert tumoral cell killing.

The $CD8^+$ cytotoxic lymphocytes (CTL) that recognize specific antigens on the cell target are depleted during antigen presentation to initiate immune reaction and also suppressed by the treatment to exert the cytotoxic activity. Amino acids such as glutamine, arginine, and citrulline are capable to enhance the metabolic pathways that generate the cytotoxic molecules produced by the CTL and hereby contribute with tumoral cell killing when tumoral antigens are more readily exposed due to the induction of cell death during treatment.

Preferably, the immunonutritional compositions according to the invention comprise at least one probiotic or a combination of probiotics. Probiotics are live microorganisms which when administered in adequate amounts confer a health benefit on the host. Probiotics may be either obtained commercially or they may be produced generally by a fermentation process and, optionally, by drying. Specific strains often have particular media or substrate preferences, which the skilled person knows about. The microorganisms may be in a dried form, or for example in a spore form for micro-organisms which form spores. The drying of micro-organisms after production by fermentation is known to the skilled person. See, e.g., EP 0 818 529 (Societe Des Produits Nestle), where a drying process of pulverisation is described, or WO 0144440 (INRA). Usually, bacterial micro-organisms are concentrated from a medium and dried by spray drying, fluidized bed drying, lyophilisation (freeze drying) or another adequate drying process. For example, micro-organisms are mixed with a carrier material such as a carbohydrate, for example sucrose, lactose or maltodextrin, a lipid or a protein, for example milk powder during or before the drying. However, the micro-organisms need not necessarily be present in a dried form. It may also be suitable to mix them directly after fermentation with a powdered nutritional composition, for example, and optionally perform a drying process, preferably at low temperatures (below 70° C.) thereafter. Such an approach is disclosed in WO 02065840 (Societe Des Produits Nestle).

A selected probiotic can be a *Bifidobacterium* or a *Lactobacillus* strain. Preferably, it is a *Bifidobacterium lactis* (German Culture Collection: DSM20215), a *Bifidobacterium longum* (CNCM 1-2170), *Lactobacillus paracasei* (CNCM 1-2116, CNCM I-1292), *Lactobacillus johnsonii* (CNCM 1-1225), *Lactobacillus salivarius, Lactobacillus reuterii* or mixtures thereof.

The term "probiotic" also includes non-replicated (dead) probiotic bacteria, fermentation substrate and/or probiotic-derived material. The immunonutritional compositions of the present invention may contain heat-killed or dead probiotics in the case of severely immunocompromised patients.

There is a general assumption that activation of protective immune responses by $CD8^+$ T cells are achieved only by live vaccines. However, antigens from killed bacteria were introduced into the major histocompatibility complex class I pathway and thus were recognized by $CD8^+$ T cells. Stimulation of protective $CD8^+$ T lymphocytes by vaccination with non-living bacteria. Szalay, G. et al., Proc. Natl. Acad. Sci. USA, 92(26):12389-12392, 1995.

Lactobacilli, such as *Lactobacillus casei*, have been shown to prevent enteric infections and stimulate IgA in malnourished animals. IgA-producing cells and T lymphocytes (TL) also increased in the large intestine during the different feeding periods. The increase of IgA may indicate that the mechanisms by which the probiotcs inhibit tumor development could be through the decrease of inflammatory response. Yogurt, in the form of a probiotic mass on the other hand, contains not only two types of bacteria—*Streptoccus thermophilus* and *Lactobacillus bulgaricus* but also bifido bacteria and sometimes *Lactobacillus casei*. Yogurt can inhibit the growth of intestinal carcinoma through increased activity of IgA, T cells and macrophages. Perdigon, G. et al., J. Dairy Sci., 78(7):1597-1606, 1995.

The daily dose of probiotics added to immunonutritional compositions of the present invention the may range from $10^7$ to $10^{10}$ CFU (colony-forming units).

The term "Active Hexose Correlated Compound (AHCC)" refers to a mixture of polysaccharides, amino acids, lipids and minerals derived from cocultured mycelia of several species of Basidiomycete mushrooms. AHCC has been implicated with immunomodulation and protection against infection. AHCC can enhance tumor immune surveillance by regulating both innate and adaptive immune responses (Gao, Y. et al., Cancer Immunol. Immunother., 55(10):1258-1266, 2006; Ritz, B. W. et al., J. Nutr. 136: 2868-2873, 2006). AHCC is commercially provided by Amino Up Chemical Co. Ltd, Japan. AHCC may increase macrophage antigen presentation activity and inhibition of tumor-derived immune suppressive factors, enhance macrophage proliferation and activation, promote differentiation of Th1 cells; increase macrophage production of IL-12, increase NK activity; promote apoptosis of cancer cells. AHCC in cancer patients has been reported to increase TNF-α, γ-interferon, interleukin-12 and decrease immunosuppressive acidic protein (IAP) and tumor growth factor (TGF)-α. In view of these possible effects of AHCC on the immune system, AHCC can be used in aiding treatment of cancer ameliorating some of the negative side effects of chemotherapy.

The term "intact protein" as used herein refers to a protein preferably not subjected to either chemical or enzymatic hydrolysis, and preferably is in a form substantially similar or identical to its natural state. According to the invention, the "intact protein" may be chosen from at least one of casein, whey protein, soy protein, collagen or wheat protein.

In the context of the present invention, the term "protein source" includes any amino-acid-based proteinogenic matter, such as intact or hydrolysed dietetic protein, as well as added peptides or free amino acids and mixtures of these, for example.

The protein source may include extensively hydrolyzed protein hydrolysates prepared from acid or enzyme treated animal and vegetable proteins, such as, casein hydrolysate, whey hydrolysate, casein/whey hydrolysate, soy hydrolysate, and mixtures thereof. By "extensively hydrolyzed" protein hydrolysates it is meant that the intact protein is hydrolyzed into peptide fragments whereby a majority of peptides fragments have a molecular weight of less than 1000 Daltons. More preferably, from at least about 75% (preferably at least about 95%) of the peptide fragments have a molecular weight of less than about 1000 Daltons. Free amino acids and synthetic short peptide chains may also be either substituted for or added to the protein hydrolysates as the nitrogen source so long as the nutritional composition has an amino acid profile suitable for the targeted population, as within the skill of one familiar with the art of nutritional formulations.

In a preferred embodiment of the immunonutritional compositions, according to the present invention, the protein source can be an animal, a plant or a vegetable protein. Accordingly, the protein source can include a combination of whey protein, casein protein or soy protein and their hydrolysates thereof.

The whey protein source may be derived from native whey, intact unhydrolyzed whey, whey protein concentrate, whey protein isolate or whey protein hydrolysate.

The casein may be provided in free form or in the form of a salt, for example, a sodium salt. It is also possible to provide the casein as a calcium or potassium-salt.

The term "amino acids" as used herein, unless otherwise stated, refers to amino acids in free form and/or in salt form chosen from at least one of essential amino acids, e.g. isoleucine, leucine, lysine, methionine, phenylalanine, threonine, tryptophan, valine, or histidine, conditionally essential amino acids, e.g. tyrosine, cysteine, arginine, or glutamine, or non-essential amino acids, e.g. glycine, alanine, proline, serine, glutamic acid, aspartic acid, asparagines, taurine or carnitine. The role of amino acids in immune function is reviewed by Peng Li and colleagues in the British J. Nutr., 98(2):237-252, 2007.

The invention also relates to immunonutritional compositions further comprising branched-chain amino acids, e.g., valine, leucine, isoleucine, or mixtures thereof, in free and/or in salt form and/or in form of intact protein. BCAAs may be in their free forms, as dipeptides, as tripeptides, as polypeptides, as BCAA-rich protein, and/or as protein manipulated to enrich the BCAA content. Dipeptides, tripeptides and polypeptides may include two or more BCAAs. Nutritional products according to the invention may similarly include precursors and/or metabolites of BCAAs.

Immune cells incorporate BCAA into proteins and are able to oxidize BCAA. The function of the immune system is to protect the host from pathogenic infectious agents and from other harmful insults. Upon infection, there is a marked increase in demand for substrates by the immune system; these substrates provide energy and are the precursors for the synthesis of new cells, effector molecules, and protective molecules. Studies have indicated that BCAA are absolutely essential for lymphocytes to synthesize protein, RNA, and DNA and to divide in response to stimulation. In mouse experiments, dietary BCAA restriction impairs several aspects of the immune function and increases the susceptibility to pathogens. Postsurgical or septic patients provided with intravenous forms of BCAA exhibited improved immunity, which may relate to improved outcome. BCAAs are therefore absolutely essential for lymphocyte responsiveness and are necessary to support other immune cell functions.

BCAA can also promote glutamine synthesis and stimulate Th1 immune response, a cellular or cell-mediated type of adaptive immune response. Intense long duration exercise has been associated with immunosuppression, which, in turn, affects natural killer cells, lymphokine-activated killer cells, and lymphocytes. Glutamine has been reported as an important fuel for macrophages and lymphocytes, presenting immunostimulatory effects. Its provision, as an oral supplement after exercise, has beneficial effects on the level of subsequent infections in endurance athletes. Plasma glutamine concentration in athletes, however, is decreased after stress, e.g., after an exercise bout. The lowering effect on glutamine concentration was abolished, however, by BCAA supplementation, which was followed by an increased proliferative response in the peripheral blood mononuclear cells. BCAA supplementation stimulated the production of IL-2 and INF after exercise and a more pronounced decrease in the production of IL-4, indicating a diversion toward a Th1 immune response. BCAA supplementation was also effective in keeping plasma glutamine concentration constant. Bassit, R. A. et al., Nutrition, 18(5):376-379, 2002.

Besides improving metabolic parameters, BCAA-enriched oral supplementation can improve morbidity and quality of life in patients undergoing major liver resection and chemo-embolization. However, the role of BCAAs in the nutritional support of stressed surgical and cancer patients remains to be clearly defined, despite their potential beneficial biological properties. Choudry, H. A. et al., J. Nutr., 136(1 Suppl.):314S-8S, 2006.

The immune response requires higher quantities of BCAA, in fact lymphocytes upon stimulation show increase uptake of BCAA for cellular expansion including leucine, isoleucine and valine. In addition, leucine is an activator of the mTOR signalling pathway that regulates protein synthesis and degradation and also that antagonizes the autophagic process of cells under stress or starvation. BCAA, when added in the immunonutritional compositions according to the present invention, in amounts that ranges from about 2 to 30 g per day, preferentially a quantity of about 3 g per day.

The immunonutritional compositions of the present invention may further comprise glutamine (Gln) and/or arginine and/or citrulline and/or branched chain amino acids (BCAA).

Glutamine is a major nutrient substrate for cells of the immune system. Besides being a major source of glutamate, Gln regulates the synthesis of glutathione and is a precursor of purine and pyrimidine nucleotides, which are required for lymphocyte proliferation. In its role in anti-cancer activity, Gln is capable of increasing the innate cytolytic activity by NK, macrophages, killer dendritic cells. Gln also contributes to the antigen-specific cytolytic activity of CD8+ T cells against tumoral cells.

Glutamine may be in the form of an added amino acid. "Added amino acid," in the context of the present invention, refers to an amino acid that is not protein-bound, but which is added separately from typical dietetic protein sources, such as milk, meat and vegetable proteins. The added amino acid may be present as a free amino acid and/or as a di- and/or tri-peptide comprising the amino acid. For example, the glutamine may be added in the form of a di-peptide such as L-alanyl glutamine. Free glutamine is not stable in a liquid environment therefore if the composition is to be sold as a liquid, glutamine will have to be added as a dipeptide or other liquid-stable form. A further possibility if the composition is to be supplied as a liquid would be for an appropriate quantity of powdered glutamine to included in modular form for mixing with the liquid immediately prior to consumption.

The amount of glutamine may range from about 5 g to about 30 g per day, more preferably from about 6 g to about 9 g per day.

In addition to the above, Gln can increase HSP expression in normal epithelial cells of the gut. The expression of HSP in tumoral cells during anti-cancer treatment may result in enhanced immunogenicity of the tumoral cells. Anti-cancer treatment induce stress on the tumor cells, which, in turn, increases the efficacy of the innate immune system to contribute to the cytotoxic effect on transformed cells and work along with the drugs in the elimination of tumor mass. The amount of Gln is preferably about 5 g to about 30 g, more preferable about 6 g to 9 g.

Arginine is synthesized from citrulline as an immediate precursor in many tissues but more importantly in the kidney. In turn citrulline is synthesize from glutamine, glutamate and proline at the gut level. Levels of citrulline and arginine decrease markedly in plasma during malnutrition, fasting, different types of injury, tumor, anti-cancer treatment and sepsis. It has been proposed that this contributes to immunodeficiency present in cancer.

The biological activities of arginine on the immune function could be categorized as direct and indirect. It can therefore be assumed that citrulline will also elicit the same effects as arginine as a result of its role in synthesis of arginine.

Many direct activities on the immune system are related to T cell function and mainly explained by the expression induction of one of the components of the T cell receptor. In fact, physiological levels of arginine (150 μM) modulates the T cell receptor chain that is required for T cell function. Interestingly citrulline has shown to have a synergistic activity with arginine for the CD3ξ chain expression prolonging the half life of its mRNA.

Several types of tumors express arginase or induce arginase expression in the immune cells resulting in one of the mechanisms underlying the immunodeficiency usually observed in the host-tumor interaction. The immunodeficiency affects CD8 antigen-specific cytotoxic function and also NK and macrophage innate cytotoxicity of transformed cells. The tumor associated macrophages have a direct participation in the immunosuppressive process by producing arginase and in addition expressing a phenotype that can induce regulatory T cells that prevents the cytotoxic activity of the immune system. These observations all together support the contention that administration of citrulline and arginine simultaneously are able to compensate for the immunodeficiency in the anti-tumoral activity.

The metabolism of L-arginine in myeloid suppressor cells is critical for the inhibition of T cell activation (Bronte, V. et al., Nat. Rev. Immunol., 5:641-654, 2005). Different metabolic pathways in the MSC have been described for the enhanced consumption of arginine and deprivation of this amino acid for T cells, a prerequisite for T cell activation. Alternatively, activated macrophages are characterized by the increased expression of arginase, an enzyme responsible for arginine depletion.

The daily dose of arginine included in the immunonutritional compositions of the present invention may range from between 5 g to about 30 g per day, preferably at a concentration range of from about 10 g to about 15 g per day.

The daily dose of citrulline included in the immunonutritional compositions of the present invention may range from between 1 g to about 30 g per day, preferably at a concentration range of from about 2 g to about 15 g per day.

Three to four grams, taken twice daily, have proven effective in various clinical applications concerning citrulline supplementation. Upon administration, results generally develop within a time period of 3-5 days. Turning now to some of the prior art, U.S. Pat. No. 5,576,351 generally describes treatment of an impaired human immune response by the administration of arginine or omithine or mixtures thereof to humans suffering from impaired immune response or at risk of suffering impaired immune response. However, there is no disclosure that any benefit in mitigating or relieving the effects of such conditions is obtained from the administration of arginine.

The invention in WO/2007/114903 provides a method and formulation for the treatment or maintenance of conditions that would be benefited from increasing or maintaining arginine levels in the blood, and having improved taste characteristics over current arginine supplementations. Further, this maintenance of arginine levels in the blood will be beneficial in acute and chronic diseases with an impaired arginine to citrulline production rate. Further the invention provides a method for treating at least one of satiety and dyspepsia in an individual. In one embodiment, the method includes administering to an individual an effective amount of L-citrulline.

As mentioned above, these two cited documents neither describe or suggest the addition of the immunonutrients to cancer patients undergoing cancer therapy-induced apoptosis, at a time when the dying tumor cells are undergoing the window of enhanced antigenic or immunogenetic expression, wherein such addition of the immunonutrients would augment or enhance the immunocompetence of the immune cells and increased immunogenecity of the tumor cells of cancer-therapy induced patients during this brief period of enhanced antigenecity.

Theanine, a non-protein amino acid that is unique to tea beverages, is the dietary source of ethylamines. Subjects administered with capsules containing theanine and cathechins showed a decreased incidence of cold and flu symptoms with an enhanced γδ T cell function. Human γδ T lymphocytes are a subset of T cells and are a first line of defense against microbes and tumors. These γδ T cells can be primed by bisphosphonates, and certain short-chain alkylamines to enhance their capacity to proliferate and to secrete cytokines upon ex vivo exposure to a wide variety of microbes and tumor cells. Ethylamine, an alkylamine, is produced by acid hydrolysis of L-theanine in the gut and by enzymatic hydrolysis mediated by amidases in the liver (Asatoor, A. M., Nature, 210(5043):1358-1360, 1966). Acid hyrdrolysed L-theanine, upon dilution in media, caused a 15-fold expansion of γδ T cells (5%-75%) from peripheral blood mononuclear cells. Bukowski, J. F. et al., Nutr. Rev., 66(2):96-102, 2008.

The compositions of the present invention may thus also be used in the preparation of nutritional formulations, medicaments or other forms of orally administered therapy for treating, preventing or alleviating side effects of radiotherapy and chemotherapy.

The immunonutritional compositions according to the invention may be produced as is conventional; for example, by blending together the protein source, the carbohydrate source, and the lipid source. Emulsifiers may be included in the blend. Vitamins and minerals may be added at this point but may also be added later to avoid thermal degradation. Any lipophilic vitamins, emulsifiers and the like may be dissolved into the lipid source prior to blending. Water, which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture.

Vitamins, such as vitamin A and its derivatives or carotenoids, have been documented to have a stimulatory effect on the immune system both in vivo and in vitro (Blomhoff, H. K. (1994) in Vitamin A in Health and Disease (Blomhoff, R., ed.), pp. 451-483, Marcel Dekker, New York) but the mechanisms responsible for such effect are not yet established. These effects may be mediated through members of retinoic acid receptors (RARs) and retinoid X receptors. For example, retinoic acid receptor-γ is dispensable for the development of immune cells, but it is required for CD8+ T cell IFN-γ production. Dzhagalov, I. et al., J. Immunol., 178(4):2113-2121, 2007. Examples of carotenoids include but are not limited to β-carotene, α-carotene, γ-carotene, lycopene, zeaxanthin, capsanthin and lutein. The immunomodulatory effect of β-carotene treatment may be attributed to pro-vitamin A properties. This observation corresponds with a previous study that was carried out in humans where an increased number of helper cells was observed and is also in agreement with experiments demonstrating an increased numbers of CD3+, CD4+ and CD8+ cells (Garcia, A. L. et al., Immunology, 110:180-187, 2003). In addition, β-carotene has been proven to enhance immune functions, via an independent pathway, i.e., enhancement of cell-surface expression of APC cells, e.g., adhesion molecules intercellular adhesion molecule-1 and leucocyte-function-associated antigen-3. Another possible mechanism involving vitamin A and its derivatives may be via the inhibitory action of β-carotene on the cyclooxygenase or lipooxygenase activities. (Garcia, A. L. et al., supra.).

The similar effects of β-carotene and carotenoids on the organs and functions of the immune system have been previously described (Bendich, A., J. Nutr., 119:112-115, 1989; Bendich, A., J. Nutr., 134:225S-230S, 2004).

Other vitamins that may have immuno-enhancing functions include vitamins D and E. For example, vitamin D is a nutrient/hormone that has been shown to regulate conventional T cell responses but not T cell development. CD d-reactive natural killer T (NKT) cells having an invariant T cell receptor Vα14 rearrangement are a unique subset of lymphocytes, which play important roles in immune regulation, tumor surveillance, and host defense against pathogens. Studies have shown that expression of the vitamin D receptor (VDR) is required for normal development and function of iNKT cells. (Yu, S. et al., Proc. Natl. Acad. Sci. USA, 105(13):5207-5212, 2008).

With respect to vitamin E, it has been reported that short term high daily dose of vitamin E treatment to cancer patients may enhance NK cell function. The amount of vitamin E given to the cancer patients was about 750 mg per day for two weeks. Hanson, M. G. et al., Cancer Immunol. Immunother., 56(7):973-984, 2007. Short-term vitamin E treatment significantly improved NK cell cytolytic activity. The increased NK cell activity in patients' peripheral blood mononuclear cells was not due to increased numbers of NK cells or an increase in the proportion of the CD56(dim) NK cell subpopulation. In addition, vitamin E treatment was associated with a small but consistent induction of NKG2D expression among all patients studied. Tumor induced immune suppression is not limited to the adaptive T cell system, and defects in dendritic cell (DC) and NK cell functions. Vitamin E has the ability to increase production of the Th1 cytokines IL-2 and IFN-gamma and to increase NK activity by a mechanism which most likely is different from the one of histamine. Hanson, M. G. et al. supra.

Proteins are milk proteins (whey or whey protein in combination with casein) and amino acids providing about 20-40% of the energy content of the product, preferentially about 30% of the product energetic content. Proteins can also include soy protein, casein protein and hydrolysates.

The lipid source may comprise saturated fatty acids (SFA), monounsaturated fatty acids (MUFA), and/or polyunsaturated fatty acids (PUFA). SFA may partially be present as medium chain triglycerides (MCT). MCT, as discussed herein, refers to triglycerides comprising $C_6$-$C_{12}$ fatty acids. The total fatty acids of the lipid source may be present in the form of n-3 fatty acids. Preferably, the n-3 fatty acid is selected from α-linolenic acid (18:3n-3), eicosapentaenoic acid (EPA, 20:5n-3), docosapentaenoic acid (DPA, 22:5n-3), or docosahexaenoic acid (DHA, 22:6n-3) or mixtures of these.

Lipids may provide an energy content ranging from 25-40% of the product, preferably from about 30% of the total energy, of which 50% are medium chain triglycerides. Polyunsaturated fatty acids (e.g., eicosapentaenoic acid (EPA) and docosahexaenoic acid (DHA)) from vegetable oils, fish oil with of n6:n3 ratio range of less than 6, preferably of about 2-3.

Essential fatty acids (EFAs) have been shown to play a role in modulating lymphocyte reactivity and destroying various tumor cells in vitro. Purasiri, P. et al., Eur. J. Surg. Oncol., 21(3):254-260. In short-term essential fatty acids (EFAs) oral supplementation (15 days), EFAs did not significantly alter NK and LAK cell cytotoxic activity in patients with localized cancer. However, in the group with advanced disease, the reduction of NK and LAK cell cytotoxic activity occurred at day 15 and steadily decline, reaching minimal levels after 6 months of supplementation. There was no change in NK and LAK cytotoxic activity in the advanced cancer group. However, long term supplementation may have detrimental effects on natural anti-cancer cytotoxic mechanisms in patients with malignant disease. Purasiri, P. et al., supra.

Examples of ω-3 fatty acids include EPA and DHA. Both EPA and DHA give rise to eicosanoids and docosanoids, respectively, which may have differing properties from arachidonic acid-derived eicosanoids. EPA and DHA give rise to resolvins. Calder, P. C. et al., Prostaglandins Leukot. Essent. Fatty Acids, 77(5-6):327-335, 2007. Resolvins, on the other hand, are known to reduce cellular inflammation by inhibiting the production and transportation of inflammatory cells and chemicals to the sites of inflammation. They have an immunological role in the kidneys as a tool against acute renal failure. Serhan, C. N. et al., J. Exp. Med., 196(8): 1025-37, 2002.

Increased incorporation of EPA into immune cell phospholipids potentially results in increased production of EPA-derived eicosanoids such as prostaglandin E3 (PGE3) and 5-series leukotrienes (LTs), since EPA can act as a substrate for cyclooxygenase and lipoxygenase enzymes. Increased generation of 5-series LTs has been demonstrated using macrophages from fish oil-fed mice, neutrophils from human subjects infused for several days with lipid emulsions containing fish oil, and neutrophils from humans supplemented with oral fish oil for several weeks.

Based on the above, fatty acids fulfill a variety of roles within immune cells. They can act as fuels for generation of energy; components of cell membrane phospholipids contributing to the physical and functional properties of those membranes; covalent modifiers of protein structure influencing the cellular location and function of proteins; regulators of gene expression either through effects on receptor activity, on intracellular signaling processes, or on transcription factor activation; and precursors for synthesis of bioactive lipid mediators like prostaglandins (PGs), leukotrienes (LTs), lipoxins and resolvins.

Changes in membrane phospholipid fatty acid composition may influence immune cell function, as illustrated hereinbelow, includes the following steps: (1) alterations in the physical properties of the membrane such as membrane order and raft structure; (2) altered effects on cell signaling pathways, either through a change in the expression, activity or avidity of membrane receptors or modifying intracellular signal transduction mechanisms; and (3) alterations in the pattern of lipid mediators (PGE2). As a result of these various changes, transcription factor activation is altered and gene expression is modified. Different mediators may lead to different biological activities and potencies. Calder, P. C. et al., supra.

Carbohydrates may provide an energy content range of about 30 and 50% of the product, preferably about 40%.

The carbohydrate source may be any suitable digestible carbohydrate or carbohydrate mixtures. For example, the carbohydrate source may be maltodextrin, native or modified starch from tapioca, corn, rice, other cereals, potato, for example, or high amylose starch, sucrose, glucose, fructose, and/or mixtures thereof.

The immunonutritional compositions according to the present invention may be clinically free of lactose. The term "clinically free of lactose" refers, in the context of the present invention, to nutritional compositions that have a maximum of 0.2 g lactose per 100 kcal of the composition. Preferably, the composition has less than 0.2, more preferably less than 0.17 g lactose per 100 kcal of the composition.

The immunonutritional compositions according to the present invention may be also be gluten-free.

The immunonutritional compositions of the present invention may also have other nutritional supplementations, for example, vitamins, minerals, trace elements, as well as additional nitrogen, carbohydrate and fatty acid sources. They can be added to the oral intake of the patient or supplied in form of a nutritional complete formulation such that the sole source of nutritional supplementing all the essential required daily amounts of vitamins, minerals, carbohydrates, fatty acids and the likes.

The immunonutritional compositions of the present invention can be formulated in a manner suitable for parenteral or enteral administration. They are particularly appropriate for enteral use, such as oral administration and/or tube feeding. Such compositions are conveniently administered in the form of an aqueous liquid. The compositions of the invention suitable for enteral application are accordingly preferably in aqueous form or in powder form, whereby the powder is conveniently added to water prior to use. For use as tube feeding, the amount of water to be added will depend on the patient's fluid requirements and condition.

The term "pharmaceutically acceptable salt" refers to those salts that are, within the scope of sound medical judgment, suitable for use in contact with the human tissue without undue toxicity, irritation, allergic response and the like and are commensurate with a reasonable benefit/risk ratio.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 5, 6, 7, from 1 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The compositions and methods of the present invention can comprise, consist of, or consist essentially of the essential elements and limitations of the invention described herein, as well as any additional or optional ingredients, components, or limitations described herein or otherwise useful in compositions and methods of the general type as described herein.

Treatment" refers to the administration of medicine or compositions or formulations or the performance of medical procedures with respect to a mammal, including a human, for either prophylaxis (prevention) or to cure or ameliorate or normalize the infirmity or malady or deficiency in the instance where the patient is afflicted or deficient.

"Patient" or "Subject" means a human or non-human mammal that may benefit from the nutritive composition and method described in the present application.

A "Therapeutically Effective Amount" or a "Nutritionally Effective Amount" is an amount of an agent, composition or formulation sufficient to achieve the desired treatment effect.

"Parenteral" refers to the route of materials across or substantially through the epidermal layers of the human body usually by means of intravenous (IV), intramuscular (IM), or subcutaneous (SC) means.

The term "enteral" as used herein refers to administration through the alimentary tract. A skilled artisan recognizes that this administration may be within the intestine, which is the tube passing from the stomach to the anus divided into the small intestine and large intestine, through the mouth, through a nasogastric tube into the stomach, and other means known in the art.

"Pharmaceutically Acceptable" means approved by a regulatory agency of the Federal or a state government or listed in the U. S. Pharmacopeia or other generally recognized pharmacopeia for use in animals, and more particularly in humans.

"Carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

As used herein, the term "cancer therapy" refers to chemotherapy, surgery, radiation, gene therapy, immunotherapy, biological therapy, differentiating agents, chemopreventive agents, or a combination thereof. In some embodiments, chemotherapy refers to drugs or agents which are cytotoxic to a cell.

As used herein, the term "chemotherapy" refers to a process of killing proliferating cells using a cytotoxic agent. The phrase "during the chemotherapy" refers to the period in which the effect of the administered cytotoxic agent lasts. On the other hand, the phrase "after the chemotherapy" is meant to cover all situations in which a composition is administered after the administration of a cytotoxic agent regardless of any prior administration of the same and also regardless of the persistence of the effect of the administered cytotoxic agent.

When the method of this invention is applied to chemotherapy, at least one immunonutritional composition can be administered prior to, during, or subsequent to the chemotherapy (i. e., prior to, during, or subsequent to the administration of a cytotoxic agent). For example, the immunonutritional compositions of the present invention can be administered to the subject from between ten and three days before one cycle of chemotherapy (pre-chemotherapy or before chemotherapy) to between ten and seven days after the cycle (post-chemotherapy or after chemotherapy).

Examples of the sweetener include, but are not limited to, saccharin sodium, aspartame, stevioside, *stevia* extract, para-methoxycinnamic aldehyde, neohesperidyl dihydrochalcone, *perilla* rutin and the like.

Useful dosage forms for pharmaceuticals include, but are not limited to, oral preparations (liquid preparations such as extracts, elixirs, syrups, tinctures, and lemonades; solid preparations such as capsules, granules, pills, powders, and tablets), injections, infusions, nasal drops, eye drops, suppositories, sprays, and dosage forms for percutaneous administration, such as ointments and patches.

According to the present invention, the compositions of the invention may be provided in form of dietary means, e.g. supplements, or in the form of a nutritional formulation, e.g. a medical food or beverage product, e.g. in form of a complete meal, part of a meal, as food additive or as powder for dissolution, or in the form of a pharmaceutical formulation, e.g. in form of a tablet, pill, sachet or capsule.

In a further aspect of the invention there is provided a medical food or beverage product, dietary supplement or nutritional or pharmaceutical formulation comprising the immunonutritional compositions of the invention.

The compositions of the invention in form of dietary means, e.g. supplements, or pharmaceutical formulations may consist exclusively of the compositions of the invention, and optionally pharmaceutically or nutritionally acceptable carriers.

The compositions of the invention may be in medical food or beverage product form, e.g. in form of a powder for dissolution. The powder may be combined with a liquid, e.g. water, or other liquid, such as milk or fruit juice, e.g. in a ratio of powder to liquid of about 1 to about 5, to obtain a ready-to-consume composition, e.g. ready-to-drink composition or instant drink.

Optionally, the compositions according to the invention may be nutritionally complete, i.e. may include vitamins, minerals, trace elements as well as nitrogen, carbohydrate and fat and/or fatty acid sources so that they may be used as the sole source of nutrition supplying essentially all the required daily amounts of vitamins, minerals, carbohydrates, fat and/or fatty acids, proteins and the like. Accordingly, the compositions of the invention may be provided in the form of a nutritionally balanced complete meal, e.g. suited for oral or tube feeding, e.g. by means of nasogastric, nasoduodenal, esophagostomy, gastrostomy, or jejunostomy tubes, or peripheral or total parenteral nutrition. Preferably the compositions of the invention are for oral administration.

The invention provides methods to support the immune system during the anti-cancer treatment either chemo- or radiotherapy.

The invention provides methods to take advantage of the increase the tumoral cell expression of cell stress molecules ("danger signal") and thereby promote the cellular recognition and killing by the innate immune cells such as natural killer cells (NK), natural killer T cells (NKT), macrophages (Macs) and killer dendritic cells (KDC). Innate immune cells become highly activated upon encounter of "danger signals" in tumoral cells during the anti-cancer treatment.

The following examples describe the presence of immune suppressor cells and immune function of tumor-bearing animals experiencing impairment of their innate and adaptive immune response, with or without undergoing chemotherapy. In addition, an example is provided that describes the beneficial effects of immunonutrition on the tumor-bearing mice undergoing anti-tumor therapy. Furthermore, five exemplary immunonutritional compositions are provided hereinbelow, all of which vary from each other in terms of the type and amount of immuno-enhancing agents present.

Example 1

Presence of Immune-Suppressor Mechanisms in Tumor-Bearing Animals—Impairment of Innate and Adaptive Immune Response.

Mice.

Inbred eight-week-old C57BL/6 (H-2b) mice were used in the experiments. Mice were inoculated subcutaneously (s.c.) on the left flank with $1 \times 10^6$ tumor cells, and tumor growth was monitored every 2 days by caliper measurement. 6 days after the tumor inoculation the animals were treated either with oxaliplatin or doxorubicin. Tumor growth was monitored every two days after the chemotherapeutic treatment and they were sacrificed after two weeks of tumor implantation. Some experiments were carried out until 28 days post-chemo to better assess tumor growth.

Body weight was assessed every two days until sacrifice.

Blood samples were obtained at day 2 and 4 after the chemo-treatment, at day 10 and at sacrifice (14 or 28 days). An autopsy was performed and tumoral mass was assessed.

Cancer Cell Lines.

Methylcholanthrene (MCA) induced sarcoma cell line expressing the exogenous antigen for ovalbumin (OVA) were grown in DMEM or RPMI 1640 supplemented with 2 mM L-glutamine, 10 mM HEPES, 20 μM 2-mercaptoethanol, 150 U/mL streptomycin, 200 U/mL penicillin, and 10% heat-inactivated FBS. $1 \times 10^6$ tumor cells were injected in the flank of the mice 6 days prior to the chemotherapy.

Haematological Evaluation.

Red blood cell enumeration, hemoglobin and hematocrit were measured at 2, 4, 10, 14 and 28 days.

White blood cell counts and differential leukocyte formulation were examined at the same time points. Blood samples were used in addition to determine immune cell populations.

Flow Cytometric Analysis.

Cell subset analysis of the $CD11c^+$, $CD11b^+Gr-1^+$ and $CD11b^+Gr-1^-$, $CD14^+$, $CD19^+$, $CD16^+$, $CD56^+$, $CD3^+$, $CD8^+$, $CD4^+$ was performed. The battery of antibodies used permitted the evaluation of: B and T cell subsets NK, NKT cells, macrophages, dendritic cells, granulocytes.

Tumor Growth Evaluation.

Growth of tumors was monitored every 2 d by using calipers, and tumor volume was calculated by using the formula length×width×width×0.52 $mm^3$.

Results.

After s.c. inoculation of tumor cells in the mice the tumors require 5 to 6 days to start growing as assessed with the caliper. The growth of tumors during the first 6 days was not associated with weight loss.

The treatment with oxaliplatin and doxorubicin at all doses tested was associated with loss of weight during the 6 days following treatment. Higher doses induced more pronounced weight loss, but most of the time weight loss was not higher than 10 or 15% of the initial body weight. Maximal weight loss was around 10 percent for all doses tested with doxorubicin (2.5, 5, 7.5 and 10 mg/kg) and around 15% with the maximal dose of oxaliplatin (10 mg/kg. Other doses tested were 5 and 7.5 mg/kg).

Those isolated animals that showed more important weight loss (beyond 15%) were sacrificed. Thereafter body weight remained stable or showed a slight recovery. In those experiments where follow up went until 28 days a new phase of weight loss started around day 20 after chemo treatment and persisted until sacrifice.

Red blood cell toxicity as assessed by the number of erythrocytes; levels of haemoglobin and hematocrit showed a distinct pattern. Both chemotherapeutic agents induced a level diminution progressing until day 6 post-chemo reaching stable levels until day 16 when the decrease started to progress again.

The white blood cell counts show a fall immediately after the chemotherapy with a recovery starting after 7 days. Interesting the oxaliplatin treated animals tended to show leukocyte counts that were higher that the baseline counts.

The flow cytometry studies of the leucocytes and immune cell subsets showed that a global diminution of the lymphocytes was induced by the chemotherapy until the day 10 post-treatment. Thereafter the number of lymphocytes started to increase and recovered the baseline line or even went beyond baseline.

The transient lymphopenia involved CD3 and CD19 (B-cells), NKs; (Ly subsets); peripheral blood includes a minority of dendritics cells and monocytes.

Tumor growth could be observed after 5-6 days of sc cell implantation. After chemotherapy tumor size does not show a significant change but growth is observed again starting around 8-10 days after the chemotherapy. Thereafter an increase of tumor size progresses until sacrifice. In the control tumor-bearing mice that were not treated with chemotherapy the pace of growth is higher until the end of the experiments (sacrifice of animals).

Figure 2:
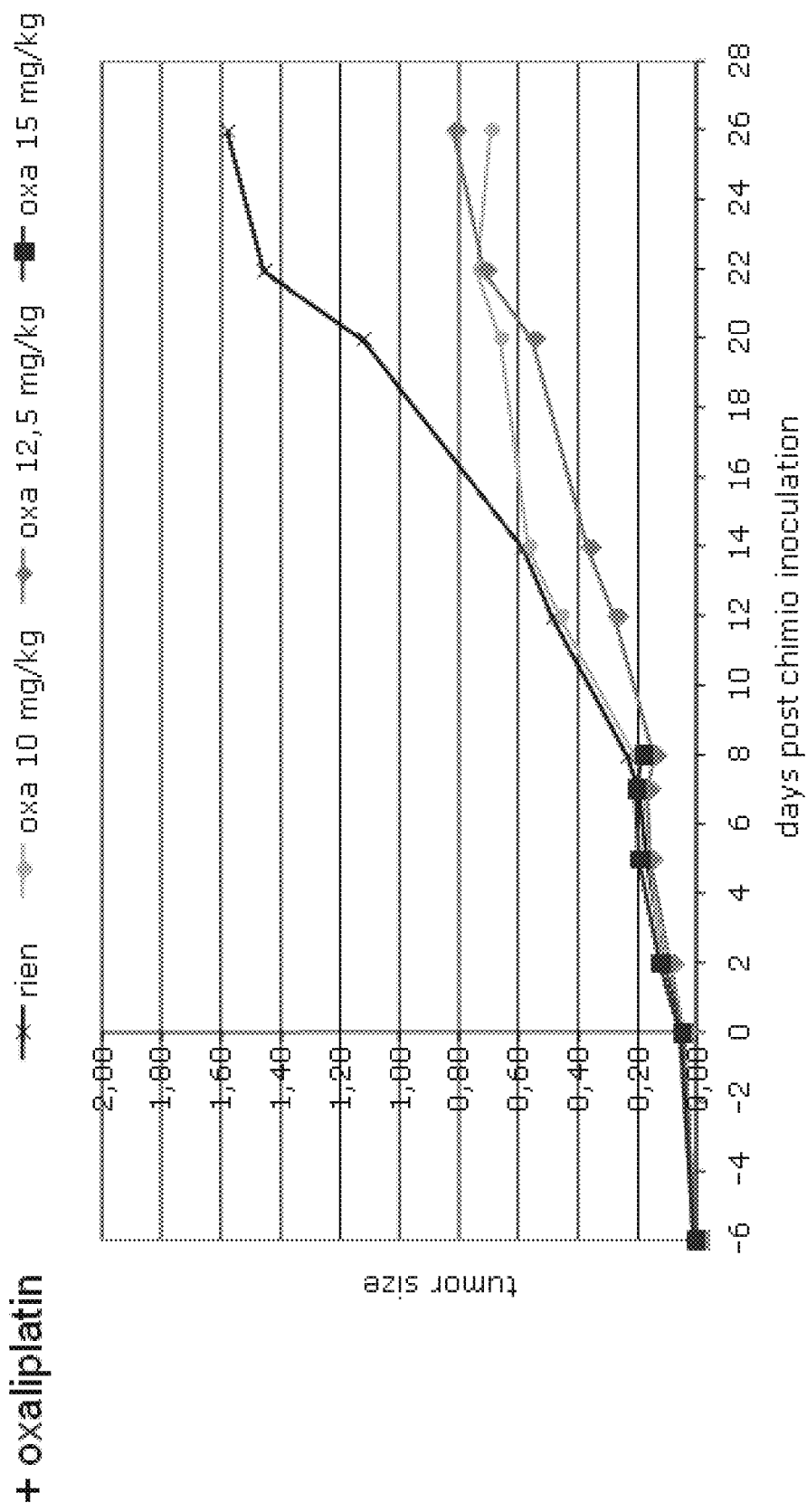
FIG. 2 illustrates a graph of the anti-tumor effect of oxaliplatin in a rodent model implanted with tumor versus control in accordance with an embodiment of the present disclosure.

FIG. 2 illustrates how the adaptive immune response is stimulated by the immunogenicity promoted by the chemotherapy treatment. Chemotherapy damages cancer cells and thus increases their susceptibility to the immune system. In FIG. 2, the divergence at day 14 of the two treatment groups (oxa-10; oxa-12.5) from the control group is related to the enhanced immune response. Although the tumor continues to grow it does so at a slower rate than the control (no chemotherapy).

Example 2

Presence of Immune-Suppressor Cell Mechanisms in Tumor-Bearing Animals Undergoing Chemotherapy. Status of the Innate and Adaptive Immune Response.

Mice.

Inbred eight-week-old C57BL/6 (H-2b) mice were used in the experiments. The animals were distributed into 7 different group diets. There was a control group that received the diet AIN 93 for adult rodents (maintenance). Test diets were administered in doses appropriate to the animal model: (a) Ctrl diet were supplemented with 1% (w/w) L-arginine, (b) 25% of the protein was replaced by glutamine, (c) 1% (w/w) L-citrulline, (d) 1 g/Kg body weight with active hexose correlated compound, (e) 20 mg/day of RNA nucleotides and (f) 25 mg/day of lactoferrin. One week later mice were inoculated subcutaneously (s.c.) on the left flank with MCA-OVA $1\times10^6$ tumor cells, and tumor growth was monitored every two days by caliper measurement. Six days after the tumor inoculation the animals were treated either with oxaliplatin or doxorubicin. Tumor growth was monitored every two days after the chemotherapeutic treatment and they were sacrificed two weeks after chemotherapeutic treatment. Control animals without chemotherapeutic treatment were run in parallel for all tested diets. Body weight was assessed every two days. Blood samples were obtained at day 2, 4 and 10 after the chemo-treatment and at sacrifice (14 or 28 days). An autopsy was performed and tumor mass was assessed.

Cancer Cell Lines.

Methylcholanthrene (MCA) induced sarcoma cell line expressing the exogenous antigen ovalbumin (OVA) was grown in DMEM or RPMI 1640 supplemented with 2 mM L-glutamine, 10 mM HEPES, 20 µM 2-mercaptoethanol, 150 U/mL streptomycin, 200 U/mL penicillin, and 10% heat-inactivated FBS. $1\times10^6$ tumor cells were injected in the flank of the mice 6 days prior to the chemotherapy.

Haematological Evaluation.

Red blood cell enumeration, hemoglobin and hematocrit were measured at 2, 4, 10, 14 and 28 days.

White blood cell counts and differential leukocyte formulation were examined at the same time points. Blood samples were used in addition to determine immune cell populations.

Flow Cytometric Analysis.

Cell subset analysis of the $CD11c^+$, $CD11b^+Gr-1^+$ and $CD11b^+Gr-1^-$, $CD14^+$, $CD19^+$, $CD16^+$, $CD56^+$, $CD3^+$, $CD8^+$, $CD4^+$ was performed. The battery of antibodies used permitted the study of B, T cell subsets NK, NKT cells, macrophages, dendritic cells, granulocytes.

Tumor Growth Evaluation.

Growth of tumors was monitored every 2 d by using calipers, and tumor volume was calculated by using the formula length×width×width×0.52 $mm^3$.

Results.

All tested diets induce a similar weight gain curve during the 8 days prior to tumour transfer. After s.c. inoculation of tumor cells in the mice the tumors require 5 to 6 days to start growing as assessed with the caliper. No alteration of tumor weight was observed after the tumor cell implantation and prior to chemotherapy. The animals lost weight during the first days post chemotherapy. Maximal weight loss was attained between days 4 and 10 post chemo and thereafter animals remained with stable weight or even started to recover body weight. No differences were observed amongst the different diets.

Maximal weight loss was around 10 percent for all doses tested with doxorubicin (2.5, 5, 7.5 and 10 mg/kg) and around 15% with the maximal dose of oxaliplatin (10 mg/kg. Other doses tested were 5 and 7.5 mg/kg).

Figure 3:
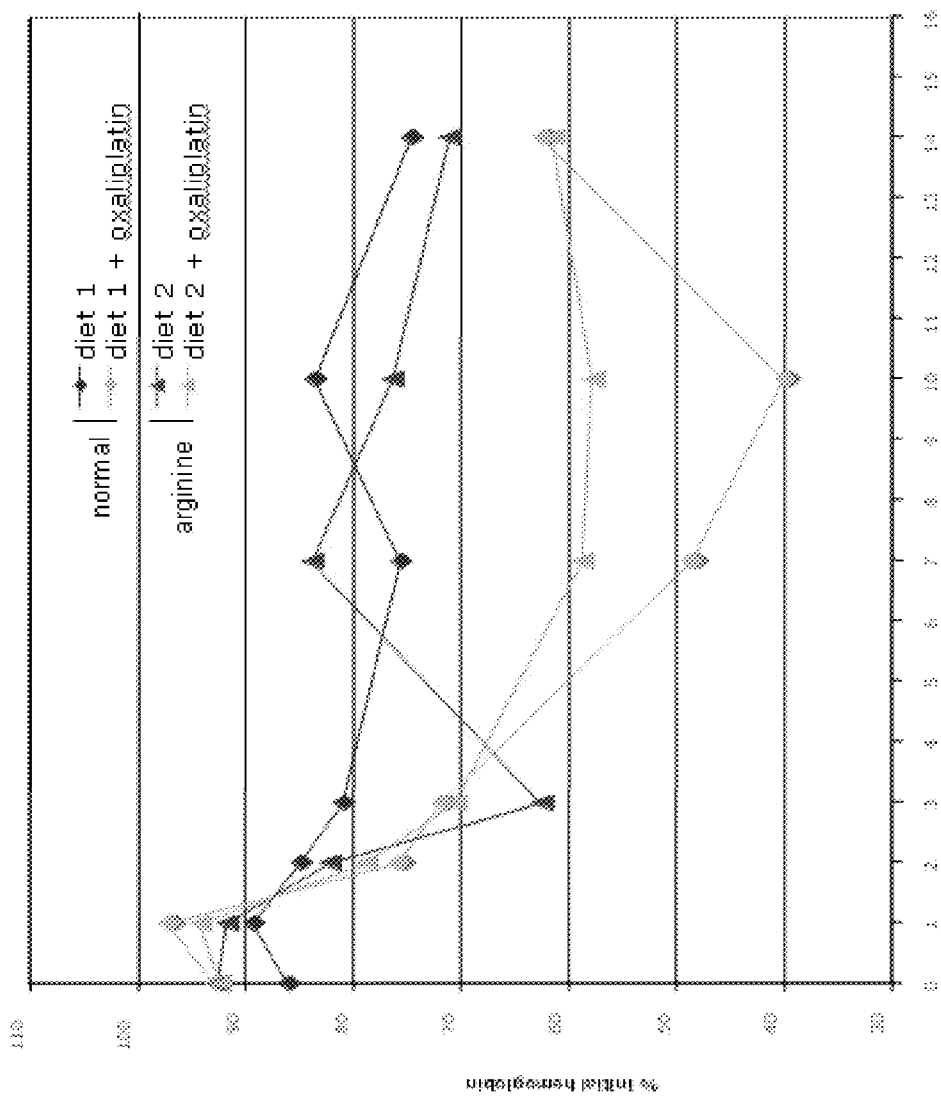
FIG. 3 illustrates a graph of the effect of dietary arginine supplementation to reduce bone marrow toxicity as compared to the control diet in the days post chemotherapy in accordance with an embodiment of the present disclosure.
Figure 4:
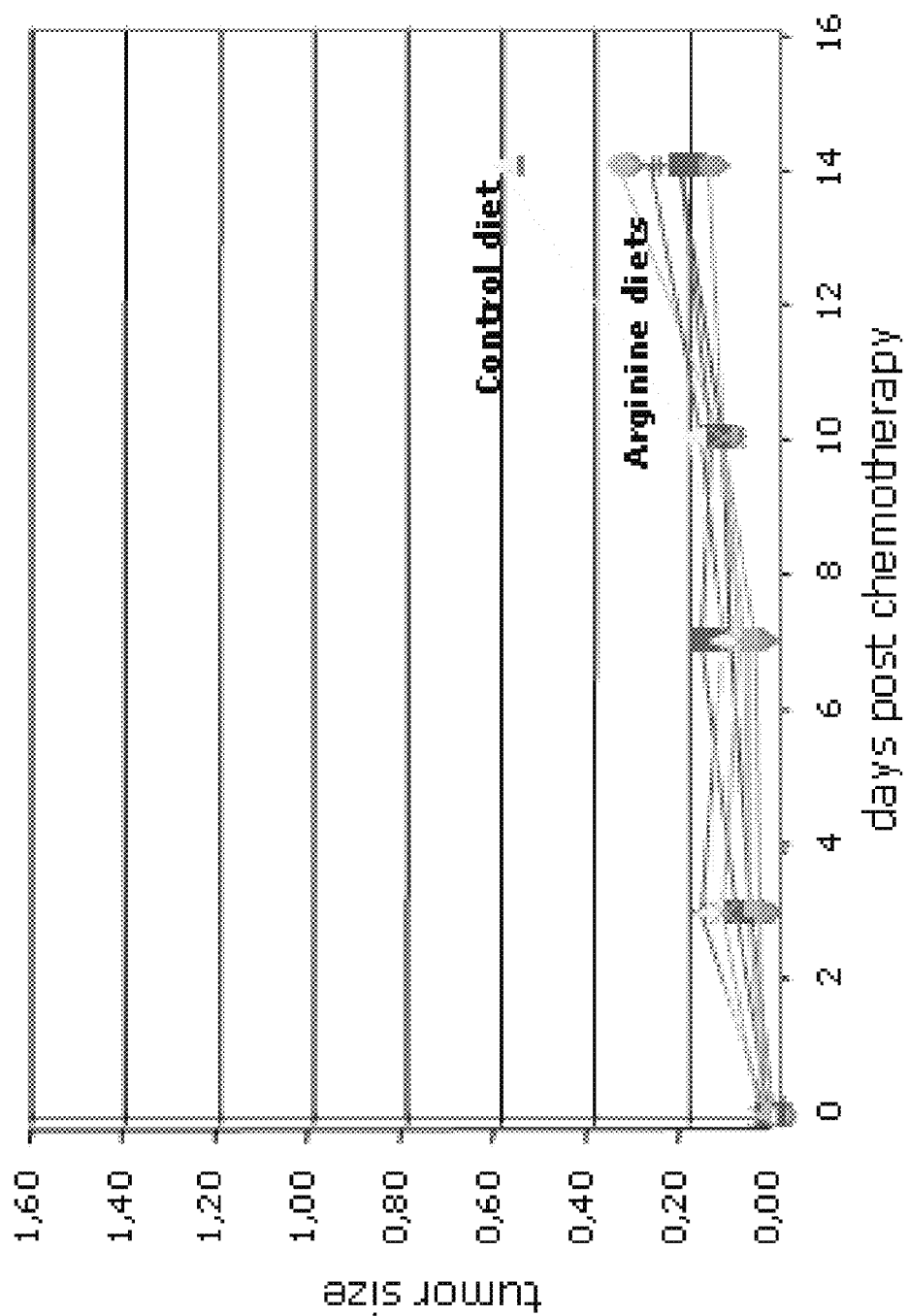
FIG. 4 illustrates a graph of the effect of dietary arginine supplementation to reduce tumor size as compared to the control diet in the days post cancer therapy in accordance with an embodiment of the present disclosure.

Red blood cell toxicity as assessed by the number of erythrocytes, levels of haemoglobin and hematocrit showed a distinct pattern. Both chemotherapeutic agents induced a decrease of RBC reaching the lowest levels between days 6 and 10 post-chemo reaching stable levels until day 16. The diet supplemented with arginine prevented the marked fall of erythrocytes observed between days 6 and 10 (FIG. 3). This group was different from the control and also the other treatments. In addition, the combination of arginine with the chemotherapy treatment further reduced the tumor size as compared to the use of chemotherapy alone (FIG. 4).

Figure 5:
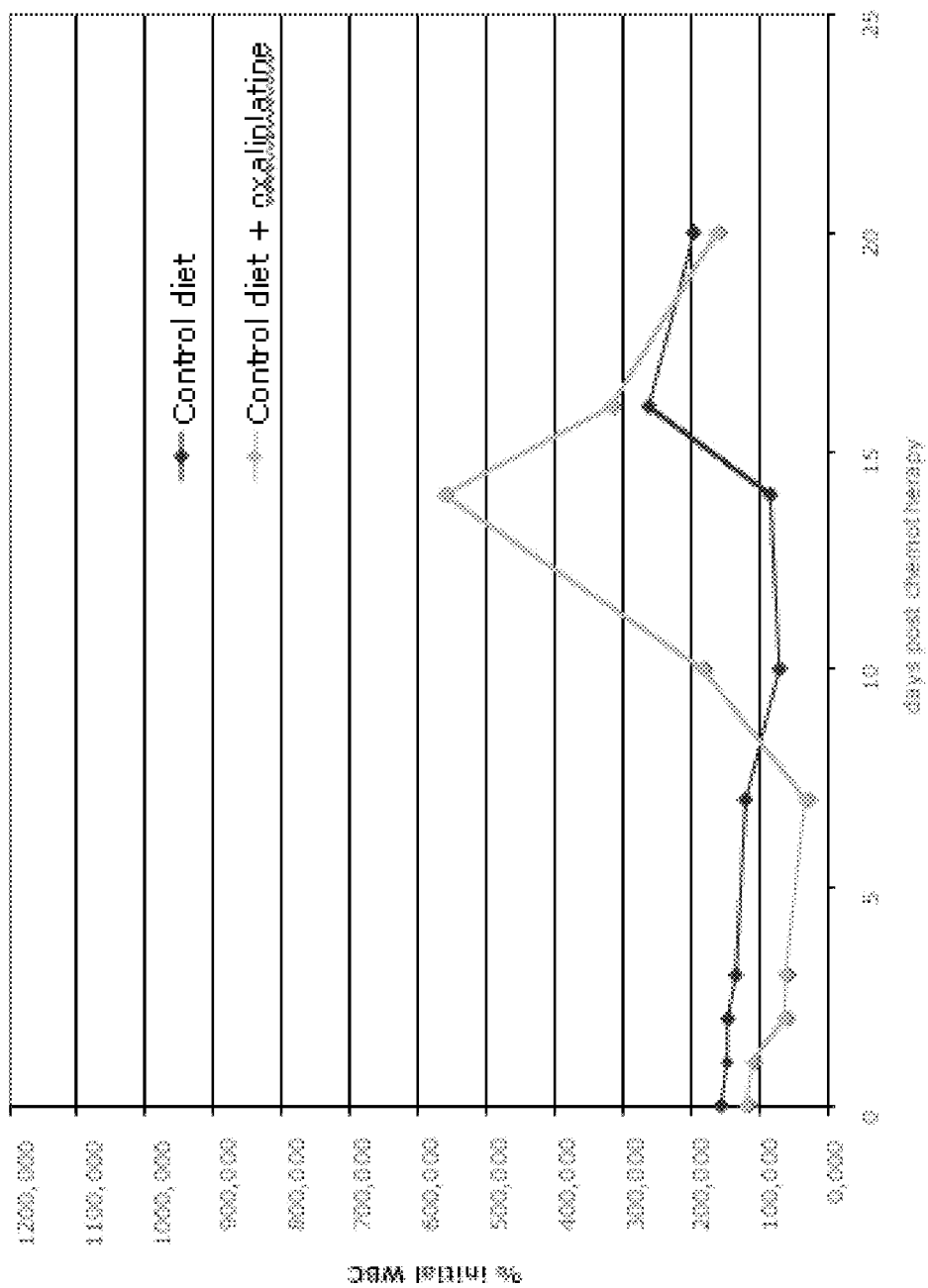
FIG. 5 illustrates a graph of the effect of oxaliplatin on white blood cell population as compared to the control diet in the days post chemotherapy in accordance with an embodiment of the present disclosure.

The white blood cell counts decreased in the first week post-chemotherapy. Before the tenth day, WBC counts start to recover and then go beyond original baseline values after day ten and tend to remain higher until the end of the experiment. The control animals that were not treated with chemo agents have a more stable level of WBC during the experiment with a trend towards an increase after day 15 (FIG. 5). In the oxaliplatin treated animals the leukocytic increase tended to be higher for the group that received the diet supplemented with lactoferrin.

Figure 6:
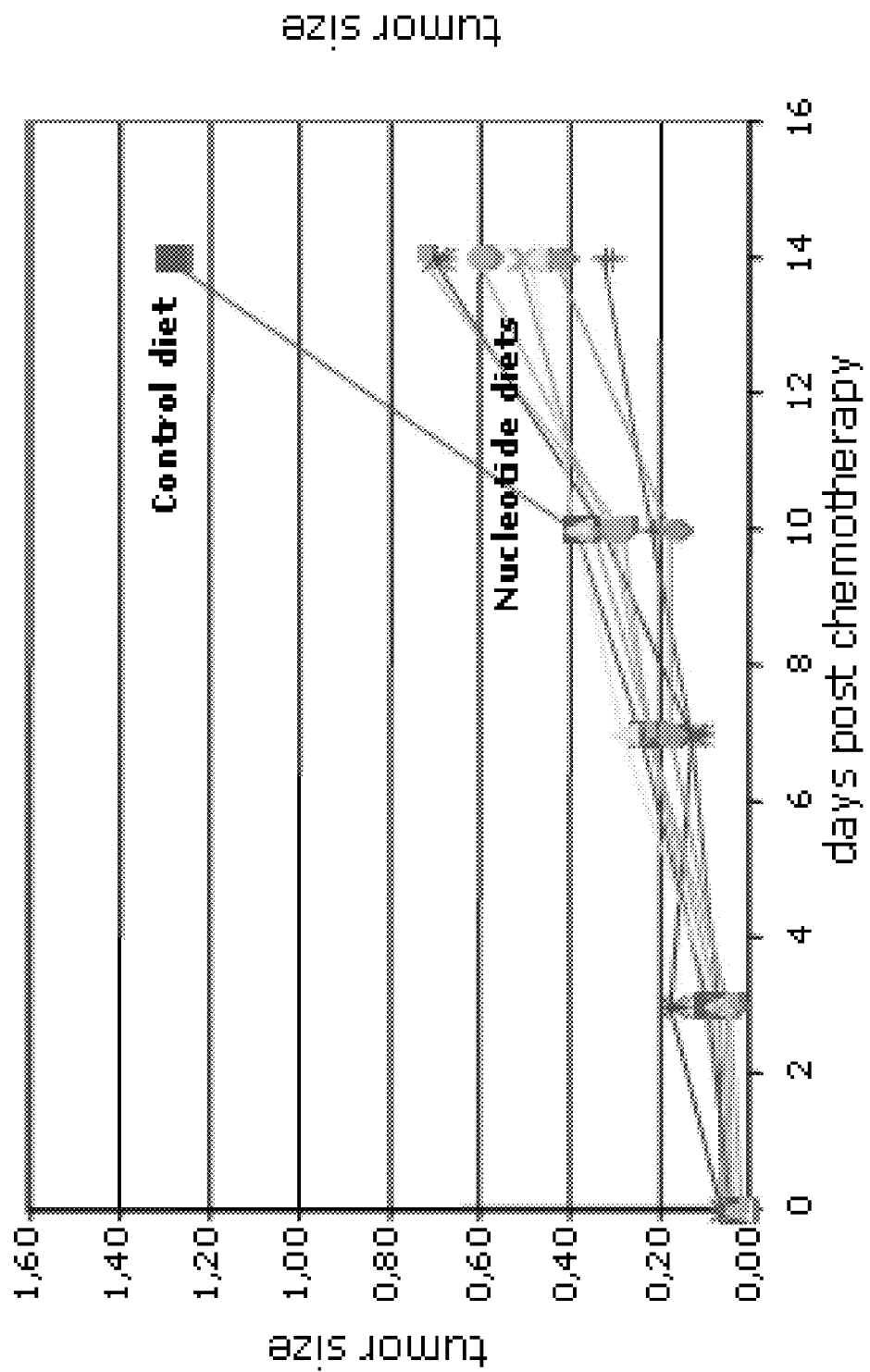
FIG. 6 illustrates a graph of the effect of dietary nucleotides to reduce tumor size as compared to control diet in the days post chemotherapy in accordance with an embodiment of the present disclosure.
Figure 7:
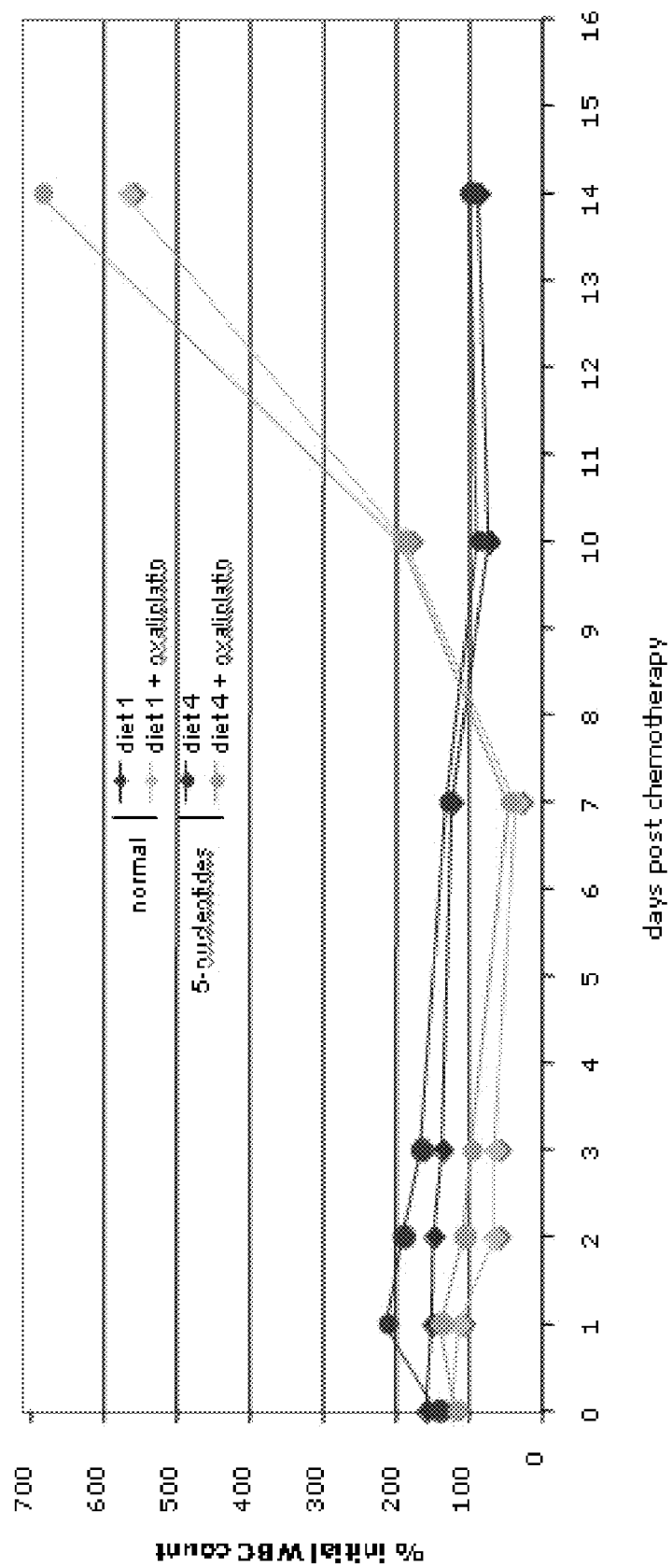
FIG. 7 illustrates a graph of the effect of dietary nucleotides on white blood cell population in early oxaliplatin-induced toxicity as compared to the control diet in the days post chemotherapy in accordance with an embodiment of the present disclosure.

The flow cytometry studies of the leukocytes and immune cell subsets showed that a global diminution of the lymphocytes was induced by the chemotherapy around 10 days post-treatment. The loss of CD3+ cells was partially modulated in the animals that received the diet supplemented with arginine. Global lymphocyte population was less depressed following chemotherapy in the groups that received the amino acids glutamine and citrulline, as well as lactoferrin. In the treatment group receiving dietary nucleotides it was observed that tumor size was reduced, even in the absence of chemotherapy (FIG. 6). In addition, the administration of dietary nucleotides also resulted in an increase in white blood cells (FIG. 7).

As previously described, tumor growth following the tumor cell transfer is also observed and can be measured by using measuring calipers after 5 to 6 days post-cell transfer. After chemotherapy, tumor growth is attenuated until approximately day 10 after the chemotherapy and thereafter there is an increase in the rate of tumor growth until the end of the experiment. In control tumor-bearing mice that were not treated with chemotherapy the pace of growth is higher until the end of the experiments (sacrifice of animals). The effect of each diet was independent on tumor growth as well as their interaction with the chemotherapeutic treatment as well as the non-treated controls. In fact the group that consumed the diet supplemented with arginine appeared to have a delayed progression of the implanted tumor as compared to other groups. In addition nucleotides seem to induce a delay in tumor growth even in the control animals that did not receive the chemotherapeutic agents.

Example 3

Presence of Immune-Suppressor Mechanisms in Tumor-Bearing Animals Undergoing Chemotherapy can be Partially Compensated by Specifically Designed Immunonutrition.

Mice.

Eight-week-old C57BU6 mice were used in the experiments. Mice were inoculated s.c. on the left flank with tumor cells, and tumor growth was monitored every 2 days by caliper measurement. An autopsy was performed between 10 and 20 days of tumor implantation and tumoral mass was assessed. Cell tumors were evaluated for the frequency of cells undergoing apoptosis, mitosis and cells going through cell cycle (Ki 67 immunohistochemical staining). Ten days after tumor implantation animals were treated with chemotherapeutic agents. The experimental animals were given 4 weekly intraperitoneal (i.p.) injections of the following drugs, individually or in combination: CYTOXAN (cyclophosphamide monohydrate), 100 mg/kg; methotrexate, RNX-0396, 25 or 50 mg/kg; ADRIAMYCIN (doxorubicin hydrochloride), 5 mg/kg; 5-FUra, 4, 25 or 50 mg/kg. Animals were sacrificed 2, 4 and 10 days after treatment administration.

Animals started the test diet 5 days before the tumor implantation. The diet was based on whey protein supplemented with glutamine, citrulline, cysteine, threonine, and arginine, nucleotides and containing $10^7$ probiotic cell counts (blend of Bifidobacteria and lactobacilli) per gram of diet. A control group of animals received normal chow.

Tissue Sampling Cell Isolation and Culture.

Tumor-bearing mice were sacrificed, and their spleens and s.c tumors were fixed in Bouin's fixative or harvested under sterile conditions. Fixed tissues were embedded in paraffin, sectioned and stained with haematoxilin and eosin or with immunohistochemical techniques to assess cell death by apoptosis and cell proliferation (Ki67). Single cell suspensions were prepared. Cell subset analysis of the $CD11b^+$ $Gr-1^+$ and $CD11b^+Gr-1^-$ cells splenocytes was performed in the spleens and tumor homogenates.

In addition, the same two cell subsets were analyzed in tissue sections of tissue-bearing tumor masses. $CD11c^+$ dendritic cells and $CD8^+$ cytotoxic lymphocytes were stained in the spleen and the tissue surrounding the implanted tumors.

$^3$H-TdR Incorporation.

$CD8^+$ T cells ($2\times10^5$ cells per well) were cultured in 96-well flat-bottom plates and stimulated with 3 µg/ml anti-CD3 and 2 µg/ml anti-CD28. $CD11b^+$ cells from tumor-bearing animals and tumor-free animals were added to the culture so as to constitute 20% of the total cells. After 2 days of incubation, cultures were pulsed with 1 µCi/well $^3$H-TdR for 18 hours, and $^3$H-TdR incorporation was measured by scintillation counting.

Evaluation of CTL Response.

To generate alloreactive CTLs, splenocytes ($3\times10^6$) from BALB/c mice-bearing tumors with the test or control diet were incubated with $3\times10^6$ γ-irradiated C57BU6 splenocytes. After 5 days, cultures were tested for ability to lyse allogenic target (MBL-2) in a 5-hour $^{51}$Cr-release assay using 2×103 target cells previously labeled with 100 µCi of $Na_2^{51}CrO_4$ for 60 minutes. The percentage of specific lysis was calculated from triplicate samples as follows: (experimental cpm−spontaneous cpm)/(maximal cpm−spontaneous cpm)×100. Lytic units (LU) were calculated as the number of cells giving 30% specific lysis of 2,000 allogeneic target cells (MBL-2 cells) per $10^6$ effector cells (LU30/$10^6$ cells). When present, the percent nonspecific lysis of CT26 control targets was subtracted from that obtained with MBL-2 target cells.

Results.

The chromiun release assay and the proliferative response in the anti-CD3 anti CD28 stimulation were higher in the tumor-bearing animals that were under chemotherapy but that received the immunonutrition diet.

Less Myeloid suppressor cells were observed in the spleen and in the peri-tumoral tissues.

Spleen and B cells from tumor bearing animals under chemotherapy consuming the test diet recovered the responsive capacity to LPS in comparison with the control group.

Overall the animals under the test diet showed an increased level of immunocompetence than those fed with the control chow diet.

Example 4

|  | 75 g powder + 180 ml water = final volume of 230 ml | 50 g powder + 120 ml water = final volume of 150 ml |
| --- | --- | --- |
| Total Energy | 350 kcal | 230 kcal |
| Total proteins (25% energy) | 21.8 g | 14.5 g |
| Casein | 7.5 g | 5 g |
| Whey protein | 7.5 g | 5 g |
| L-glutamine | 6.8 g | 4.5 g |
| Carbohydrates (40% energy) | | |
| Corn syrup | 35.3 g | 23.5 g |
| Lactose | 0.06 g | 0.04 g |
| Lipids (35% energy) | 13.7 g | 9.1 g |
| Medium chain triglycerides | 6.8 g | 4.6 g |
| Linoleic acid | 2.3 g | 1.7 g |
| α-LINOLENIC ACID | 420 mg | 315 mg |
| Fatty acids | 705 mg | 470 mg |
| n6/n3 ratio | 3.50 | |
| Minerals | | |
| Sodium | 0.18 g | 0.12 g |
| Chloride | 173 mg | 115 mg |
| Potassium | 390 mg | 260 mg |
| Calcium | 225 mg | 150 mg |
| Phosphorous | 180 mg | 120 mg |
| Magnesium | 36 mg | 24 mg |
| Iron | 4.2 mg | 2.8 mg |
| Zinc | 3.3 mg | 2.2 mg |
| Copper | 0.38 mg | 0.26 mg |
| Iodine | 45 μg | 30 μg |
| Selenium | 15 μg | 10 μg |
| Manganese | 0.83 mg | 0.55 mg |
| Chromium | 24 μg | 15.5 μg |
| Molybdenum | 29 pg | 19.5 pg |
| Vitamins | | |
| Vitamin C | 42 mg | 27.5 mg |
| Vitamin E mg α-TE (IU) | 6.2 (9.3) | 4.2 (6) |
| Vitamin A μg RE (IU) | 290 (970) | 195 (650) |
| Vitamin D μg (IU) | 3.8 (150) | 2.6 (100) |
| Vitamin K μg | 19 | 12.5 |
| Thiamine mononitrate (Vitamin $B_1$) mg | 0.55 | 0.37 |
| Riboflavin (Vitamin $B_2$) mg | 0.52 | 0.35 |
| Pyridoxine (Vitamin $B_6$) mg | 0.9 | 0.6 |
| Niacin mg (mg NE) | 5.3 (9) | 3.5 (6) |
| Folic Acid μg | 110 | 75 |
| Vitamin $B_{12}$ (cyanocobalamin) mg | 1.1 | 0.75 |
| Pantothenic Acid mg | 1.9 | 1.3 |
| Biotin mg | 0.012 | 0.008 |

Example 5

| | 75 g powder + 180 ml water = final volume of 230 ml | 50 g powder + 120 ml water = final volume of 150 ml |
|---|---|---|
| Total energy | 350 kcal | 230 kcal |
| Total proteins (25% energy) | 21.8 g | 14.5 g |
| Whey Protein | 7.5 g | 5 g |
| L-Glutamine | 6.8 g | 4.5 g |
| L-Arginine | 7.5 g | 5 g |
| Carbohydrates (40% energy) | | |
| Corn Syrup | 35.3 g | 23.5 g |
| Lactose | 0.06 g | 0.04 g |
| Lipids (35% energy) | 13.7 g | 9.1 g |
| Medium Chain Triglyceride | 6.8 g | 4.6 g |
| Linoleic Acid | 2.3 g | 1.7 g |
| α-Linolenic Acid | 420 mg | 315 mg |
| Fatty Acids | 705 mg | 470 mg |
| n6/n3 Ratio | 3.50 | |
| Minerals | | |
| Sodium | 0.18 g | 0.12 g |
| Chloride | 173 mg | 115 mg |
| Potassium | 390 mg | 260 mg |
| Calcium | 225 mg | 150 mg |
| Phosphorous | 180 mg | 120 mg |
| Magnesium | 36 mg | 24 mg |
| Iron | 4.2 mg | 2.8 mg |
| Zinc | 3.3 mg | 2.2 mg |
| Copper | 0.38 mg | 0.26 mg |
| Iodine | 45 μg | 30 μg |
| Selenium | 15 μg | 10 μg |
| Manganese | 0.83 mg | 0.55 mg |
| Chromium | 24 μg | 15.5 μg |
| Molybdenum | 29 pg | 19.5 pg |
| Vitamins | | |
| Vitamin C | 42 mg | 27.5 mg |
| Vitamin E mg α-TE (IU) | 6.2 (9.3) | 4.2 (6) |
| Vitamin A μg RE (IU) | 290 (970) | 195 (650) |
| Vitamin D μg (IU) | 3.8 (150) | 2.6 (100) |
| Vitamin K μg | 19 | 12.5 |
| Thiamine mononitrate (Vitamin $B_1$) mg | 0.55 | 0.37 |
| Riboflavin (Vitamin $B_2$) mg | 0.52 | 0.35 |
| Pyridoxine (Vitamin $B_6$) mg | 0.9 | 0.6 |
| Niacin mg (mg NE) | 5.3 (9) | 3.5 (6) |
| Folic Acid μg | 110 | 75 |
| Vitamin $B_{12}$ (cyanocobalamin) mg | 1.1 | 0.75 |
| Pantothenic Acid mg | 1.9 | 1.3 |
| Biotin mg | 0.012 | 0.008 |

Example 6

| | 75 g powder + 180 ml water = final volume of 230 ml | 50 g powder + 120 ml water = final volume of 150 ml |
|---|---|---|
| Total energy | 350 kcal | 230 kcal |
| Total proteins (25% energy) | 21.8 g | 14.5 g |
| Whey Protein | 7.5 g | 5 g |
| L-Glutamine | 5.8 g | 3.9 g |
| L-Arginine | 5.5 g | 3.7 g |
| L-Leucine | 3.0 g | 2.0 g |
| Carbohydrates (40% energy) | | |
| Corn Syrup | 35.3 g | 23.5 g |
| Lactose | 0.06 g | 0.04 g |
| Lipids (35% energy) | 13.7 g | 9.1 g |
| Medium Chain Triglycerides | 6.8 g | 4.6 g |
| Linoleic Acid | 2.3 g | 1.7 g |
| α-Linolenic Acid | 420 mg | 315 mg |
| Fatty Acids | 705 mg | 470 mg |
| n6/n3 Ratio | 3.50 | |
| Minerals | | |
| Sodium | 0.18 g | 0.12 g |
| Chloride | 173 mg | 115 mg |
| Potassium | 390 mg | 260 mg |
| Calcium | 225 mg | 150 mg |
| Phosphorous | 180 mg | 120 mg |
| Magnesium | 36 mg | 24 mg |
| Iron | 4.2 mg | 2.8 mg |
| Zinc | 3.3 mg | 2.2 mg |
| Copper | 0.38 mg | 0.26 mg |
| Iodine | 45 μg | 30 μg |
| Selenium | 15 μg | 10 μg |
| Manganese | 0.83 mg | 0.55 mg |
| Chromium | 24 μg | 15.5 μg |
| Molybdenum | 29 pg | 19.5 pg |
| Vitamins | | |
| Vitamin C | 42 mg | 27.5 mg |
| Vitamin E mg α-TE (IU) | 6.2 (9.3) | 4.2 (6) |
| Vitamin A μg RE (IU) | 290 (970) | 195 (650) |
| Vitamin D μg (IU) | 3.8 (150) | 2.6 (100) |
| Vitamin K μg | 19 | 12.5 |
| Thiamine mononitrate (Vitamin $B_1$) mg | 0.55 | 0.37 |
| Riboflavin (Vitamin $B_2$) mg | 0.52 | 0.35 |
| Pyridoxine (Vitamin $B_6$) mg | 0.9 | 0.6 |
| Niacin mg (mg NE) | 5.3 (9) | 3.5 (6) |
| Folic Acid μg | 110 | 75 |
| Vitamin $B_{12}$ (cyanocobalamin) mg | 1.1 | 0.75 |
| Pantothenic Acid mg | 1.9 | 1.3 |
| Biotin mg | 0.012 | 0.008 |

Example 7

| | 75 g powder + 180 ml water = final volume of 230 ml | 50 g powder + 120 ml water = final volume of 150 ml |
|---|---|---|
| Total energy | 350 kcal | 230 kcal |
| Total proteins (25% energy) | 21.8 g | 14.5 g |
| Whey protein | 7.5 g | 5 g |
| L-Glutamine | 5.8 g | 3.9 g |
| L-Arginine | 5.5 g | 3.7 g |
| L-Leucine | 3.0 g | 2.0 g |
| Carbohydrates (40% energy) | | |
| Corn syrup | 35.3 g | 23.5 g |
| Lactose | 0.06 g | 0.04 g |
| Lipids (35% energy) | 13.7 g | 9.1 g |
| Medium chain triglycerides | 6.8 g | 4.6 g |
| Linoleic acid | 2.3 g | 1.7 g |
| α-Linolenic acid | 420 mg | 315 mg |
| Fatty acids | 705 mg | 470 mg |
| n-6/n3 ratio | 3.50 | |
| Minerals | | |
| Sodium | 0.18 g | 0.12 g |
| Chloride | 173 mg | 115 mg |
| Potassium | 390 mg | 260 mg |
| Calcium | 225 mg | 150 mg |
| Phosphorous | 180 mg | 120 mg |
| Magnesium | 36 mg | 24 mg |
| Iron | 4.2 mg | 2.8 mg |
| Zinc | 3.3 mg | 2.2 mg |
| Copper | 0.38 mg | 0.26 mg |
| Iodine | 45 μg | 30 μg |
| Selenium | 15 μg | 10 μg |
| Manganese | 0.83 mg | 0.55 mg |
| Chromium | 24 μg | 15.5 μg |
| Molybdenum | 29 pg | 19.5 pg |
| Vitamins | | |
| Vitamin C | 42 mg | 27.5 mg |
| Vitamin E mg α-TE (IU) | 6.2 (9.3) | 4.2 (6) |
| Vitamin A μg RE (IU) | 290 (970) | 195 (650) |
| Vitamin D μg (IU) | 3.8 (150) | 2.6 (100) |
| Vitamin K μg | 19.0 | 12.5 |
| Thiamine mononitrate (Vitamin $B_1$) mg | 0.55 | 0.37 |
| Riboflavin (Vitamin $B_2$) mg | 0.52 | 0.35 |
| Pyridoxine (Vitamin $B_6$) mg | 0.9 | 0.6 |
| Niacin mg (mg NE) | 5.3 (9) | 3.5 (6) |
| Folic Acid μg | 110 | 75 |
| Vitamin $B_{12}$ (cyanocobalamin) mg | 1.1 | 0.75 |
| Pantothenic Acid mg | 1.9 | 1.3 |
| Biotin mg | 0.012 | 0.008 |
| Probiotics | | |
| Lactobacilli/Bifidobacteria | $10^9$ CFU | $10^9$ CFU |

Example 8

| | 75 g powder + 180 ml water = final volume of 230 ml | 50 g powder + 120 ml water = final volume of 150 ml |
|---|---|---|
| Total energy | 350 kcal | 230 kcal |
| Total proteins (25% energy) | 21.8 g | 14.5 g |
| Whey protein | 7.5 g | 5 g |
| L-Glutamine | 5.8 g | 3.9 g |
| L-Arginine | 5.5 g | 3.7 g |
| L-Leucine | 3.0 g | 2.0 g |
| Carbohydrates (40% energy) | | |
| Corn Syrup | 35.3 g | 23.5 g |
| Lactose | 0.06 g | 0.04 g |
| Lipids (35% energy) | 13.7 g | 9.1 g |
| Medium Chain Triglycerides | 6.8 g | 4.6 g |
| Linoleic Acid | 2.3 g | 1.7 g |
| α-Linolenic Acid | 420 mg | 315 mg |
| Fatty Acids | 705 mg | 470 mg |
| n-6/n3 ratio | 3.50 | |
| Minerals | | |
| Sodium | 0.18 g | 0.12 g |
| Chloride | 173 mg | 115 mg |
| Potassium | 390 mg | 260 mg |
| Calcium | 225 mg | 150 mg |
| Phosphorous | 180 mg | 120 mg |
| Magnesium | 36 mg | 24 mg |
| Iron | 4.2 mg | 2.8 mg |
| Zinc | 3.3 mg | 2.2 mg |
| Copper | 0.38 mg | 0.26 mg |
| Iodine | 45 μg | 30 μg |
| Selenium | 15 μg | 10 μg |
| Manganese | 0.83 mg | 0.55 mg |
| Chromium | 24 μg | 15.5 μg |
| Molybdenum | 29 pg | 19.5 pg |
| Vitamins | | |
| Vitamin C | 42 mg | 27.5 mg |
| Vitamin E mg α-TE (IU) | 6.2 (9.3) | 4.2 (6) |
| Vitamin A μg RE (IU) | 290 (970) | 195 (650) |
| Vitamin D μg (IU) | 3.8 (150) | 2.6 (100) |
| Vitamin K μg | 19 | 12.5 |
| Thiamine Mononitrate (vitamin $B_1$) mg | 0.55 | 0.37 |
| Riboflavin (Vitamin $B_2$) mg | 0.52 | 0.35 |
| Pyridoxine (Vitamin $B_6$) mg | 0.9 | 0.6 |
| Niacin mg (mg NE) | 5.3 (9) | 3.5 (6) |

| | 75 g powder + 180 ml water = final volume of 230 ml | 50 g powder + 120 ml water = final volume of 150 ml |
|---|---|---|
| Folic acid µg | 110 | 75 |
| Vitamin $B_{12}$ (Cyanocobalamin) µg | 1.1 | 0.75 |
| Pantothenic Acid mg | 1.9 | 1.3 |
| Biotin mg | 0.012 | 0.008 |
| Probiotics | | |
| Lactobacilli/ Bifidobacteria | $10^9$ CFU | $10^9$ CFU |
| Nucleotides | | |
| RNA/DNA | 1.5 g | 1.0 g |

Examples of Clinical Evidences of Nutritional Intervention to Prevent and/or Moderate Bone Marrow Paralysis, and Especially Neutropenia, Induced by Anti-Cancer Treatment.

Febrile neutropenia and infection is a frequent complication in patients treated for malignancies. The prevention of neutropenia, febrile neutropenia and infection result in the improvement of quality of life, adherence to treatment protocol, tumor response to treatment, freedom from treatment failure and overall survival and other adverse effects. The application of the intended dose on the foreseen time shall improve tumor response to treatment and survival; in contrast reduction of the dose intensity or the prolongation in time are undesirable.

Myelosuppressive effect of cytotoxic drugs during Hodgkin's disease treatment. Treatment with growth factors and secondary prevention with immunonutritional support.

Secondary Prophylaxis.

Case Report.

A patient of 26 years of age is diagnosed with Hodgkin's disease (HD), mixed cellularity variant after two months of recurrent fever and weight loss. Two cervical adenopathies are discovered during the first clinical examination and in the biopsies the histological diagnosis is HD, mixed cellularity variant. Multiple mediastinal adenopathies are observed under x-ray and scanner examination. No subdiaphragmatic involvement could be detected by imagery. The patient is treated with a standard chemotherapy protocol including ADRIAMYCIN (doxorubicin hydrochloride), bleomycin, vinblastine, dacarbazine (ABVD). 15 days after the initial treatment the patient presented with fever, low white blood cells counts, and important neutropenia (800/µL). The patient was treated with a combination of antibiotics and granulocyte colony stimulating factor. 4 weeks later the patient was going to be submitted to the next chemotherapy cycle and the leucocyte formula was within normal limits with 5500 granulocytes/µL. One week before the treatment the patient receives a daily supplement containing: 12.5 g of arginine, 3.3 g of n-3 fatty acids, and 1.2 g of RNA the patient is given an oral supplement in one liter. The patient is advised to have a liter of the product in addition to her normal diet.

The nutritional supplement attenuates the chemotherapy-induced neutropenia and the patient has a reduced or no need to be treated with granulocyte-colony stimulating factor. Same nutritional intervention is repeated prior to the following cycles of chemotherapy and only minor neutropenic responses are observed that will not require additional growth factor treatments or delay in treatment.

Gastrointestinal and Bone Marrow Toxicities of Cytotoxic Drugs Against Solid Tumors. Primary Prevention with Immunonutritional Support. Experimental Studies.

Mice (20 per group) bearing subcutaneous human colon DLD-1 tumors are injected intraperitoneally (tumoral implantation is day 1 in the experimental chart) with 5-fluorouracil (50 mg/kg) on days 17, 24 and 31 after tumor cell implants. On day 10 after tumor implantation the animals are started on a nutritional intervention that consisted of a complete controlled diet supplemented with arginine, n-3 fatty acids and nucleotides. A control group of animals that followed a similar protocol are administered with a complete controlled diet devoid of free arginine, n-3 FA and nucleotides. Survival and body weight was daily monitored. Blood was taken for full blood count and differential white cell counts at days 20 and 33. The tumor weight was assessed at the end of the experiment on day 35.

The animal survival is of 75% in the test diet group and 66% in the control diet group. The animal death is not due to tumor growth but is interpreted to be the result of the drug toxicity. In fact tumor weight does not increase during the study it decreases and there is a trend to find smaller remaining tumoral masses in the animals consuming the test diet supplemented with the immuno-nutrients (−25% vs-18% compared with tumor weight just prior to initiation of chemotherapy). The differences does not attain statistical significance. Peripheral blood elements are measured on day 20 and 33. At day 20 there is a fall in neutrophil counts that reached 50% of the average values registered at day 16 (one day prior to the anti-tumor treatment) in the control group and of 28% in the animals receiving the test diet supplemented with immunonutrients. Changes in the thrombocyte number is not different between groups and attained 20%.

The intestinal histopathology shows moderate changes in the animals at the moment of the sacrifice which include villus shortening and fusion, lower mitotic activity in the crypts and higher inflammatory infiltration in the lamina propria. In the group that receives the test diet, the intestinal damage was milder.

Gastrointestinal and Bone Marrow Toxicities of Cytotoxic Drugs Against Head and Neck Experimental Cancer. Primary Prevention with Immunonutritional Support.

Male CB6F1-Tg rasH2@Jcl mice (Tg) at 8 weeks of age are obtained and maintained in plastic cages. They are all allowed free access to a powdered basal diet of CRF (Charles River Formula)-1. A carcinogen, 4-nitroquinoline 1-oxide is used to induce tongue and/or esophageal tumors in this study.

100% of the mice develop tumors (even multiple tumors) on the tongue, 60% develop tumors in the esophagus. Several dysplastic lesions are observed in the areas that are not macroscopically showing tumoral lesions.

Animals with tongue and esophagus tumors are retained for the rest of the experiment. They start treatment with a combination of cisplatin, paclitaxel and doxorubicin. 7 days prior to the first cycle of the chemotherapeutic treatment animals are randomized in two groups: one that receives a diet supplemented with arginine, n-3 fatty acids and nucleotides whereas a control group is nourished with an isocaloric, isonutrogenous diet devoid of free arginine, n-3 fatty acids and nucleotides. 3 cycles 2 weeks apart from each other were performed. The nutritional interventions are pursued throughout the study until day 55 when animals are sacrificed. Peripheral blood cells were studies 10 days after $1^{st}$ and $2^{nd}$ cycle and before sacrifice. Neutrophil counts are 43% of the average values registered the day before starting the chemotherapy in the control group and of 70% in the animals receiving the test diet supplemented with immunonutrients. No differences in tumor regression is observed between the two different diet groups. In both a reduction of tumoral mass is measured. The histological study of the remaining macroscopic tumoral lesions and dysplastic lesions shows a similar mitotic activity or cells going into cell cycle (PCNA labeling index).

Figure 8:
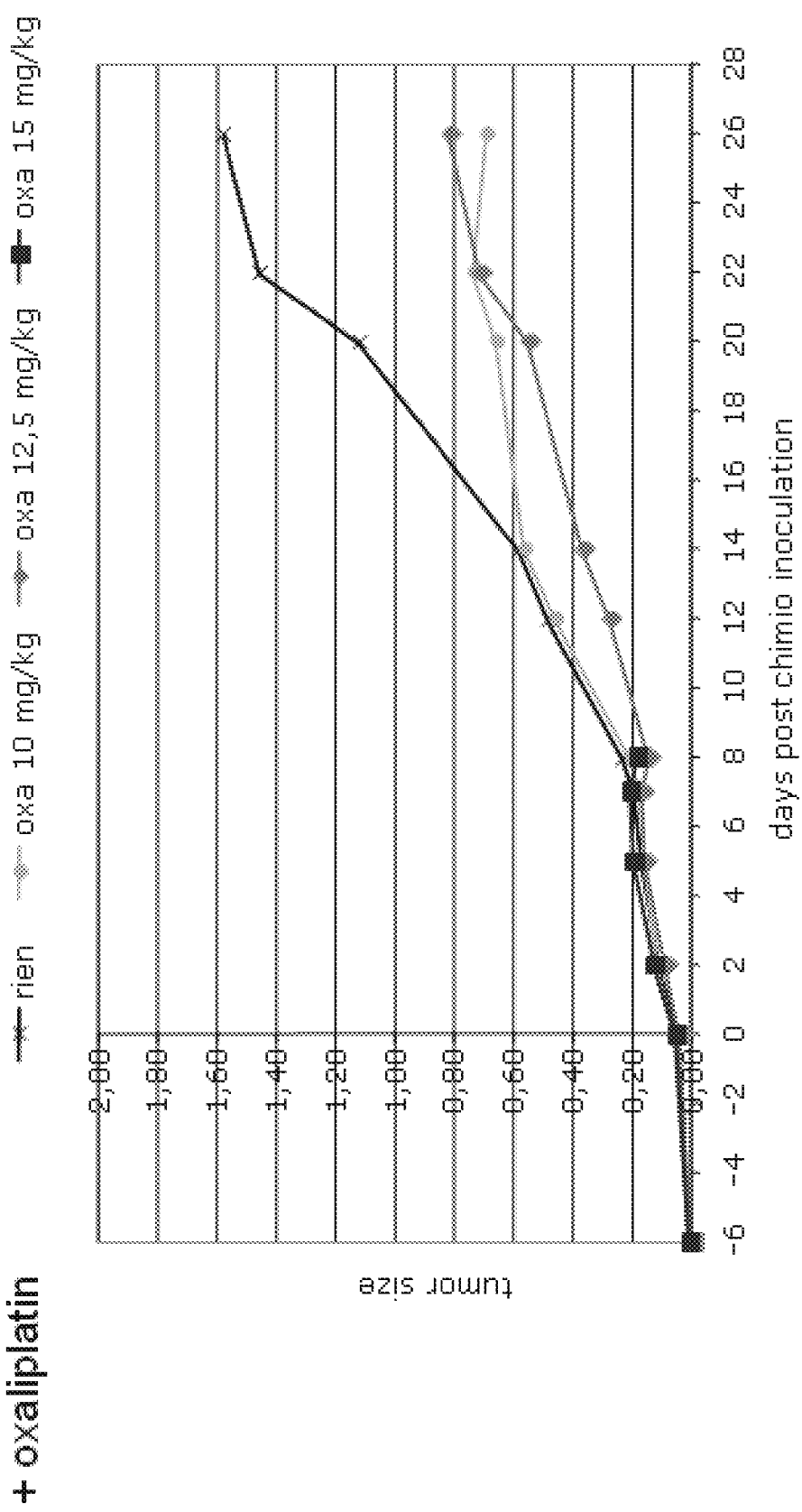
FIG. 8 illustrates a graph of the anti-tumor effect of oxaliplatin in a rodent model implanted with a tumor in accordance with an embodiment of the present disclosure.

Treatment of Bone Marrow and Immune Compartment Toxicities Caused by Both the Cancer Therapy and the Tumor Maintenance of immunocompetence during cancer treatment increases the ability of the body to naturally identify and destroy cancerous cells in the body. As a result, any insult to those compartments involved in the production, maturation, or maintenance of the immune system increases the risk of cancer progression. Chemicals and radiological treatment are designed to destroy cancer cells; some of which are very effective at reducing the growth rate of tumors (FIG. 8).

The slowing of tumor growth, or even reduction of tumor size, through the aggressive use of chemo- and/or radio-therapies is part of the neoadjuvant strategy prior to surgical intervention. However, anti-cancer therapies are equally likely to negatively influence other rapidly-dividing cells produced, by the bone marrow for example, as they are to destroy cancer cells.

Because the bone marrow is the site where blood cells are manufactured, the toxicity (for any reason) results in a deficiency of blood cells. A result of this bone marrow toxicity includes life-threatening infection because the body cannot produce leukocytes in response to invading bacteria and viruses. In addition, toxicity results in anemia due to low red blood cell numbers and even severe bleeding caused by a deficiency of platelets.

As described previously, cancer cells which are damaged by the neoadjuvant treatment may express components recognized by the immune system, but the body can only mount a response when the immune system is not too severely compromised by the same cancer therapy. Therefore, it is necessary to maintain immunocompetence through reduced bone marrow toxicity to increase efficacy of treatment. The 'window of opportunity' for the immune system to recover the control on the transformed cells and suppress remaining tumor cells occurs in the days following chemotherapy. In order to take advantage of this period of enhanced antigenic or immunogenic expression, the present invention describes methods (nutritional and other) that may enhance the innate immune response and anti-tumor immune response. Selective use of nutrition (but also pharmaceutical compounds) to condition the immune system prior to, during, and after the cycles of chemo- and radiotherapy treatment can correct acute immune toxicities induced by these cancer therapies.

Figure 9:
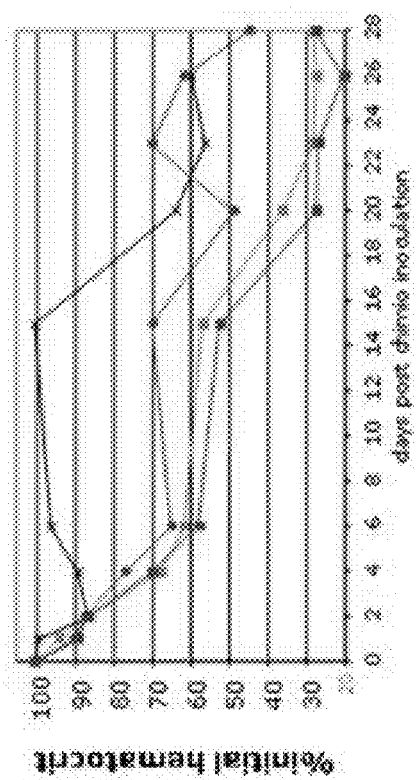
FIG. 9 illustrates a graph of the effect of doxorubicin on bone marrow products in animals implanted with tumor and controls in accordance with an embodiment of the present disclosure.
Figure 9:
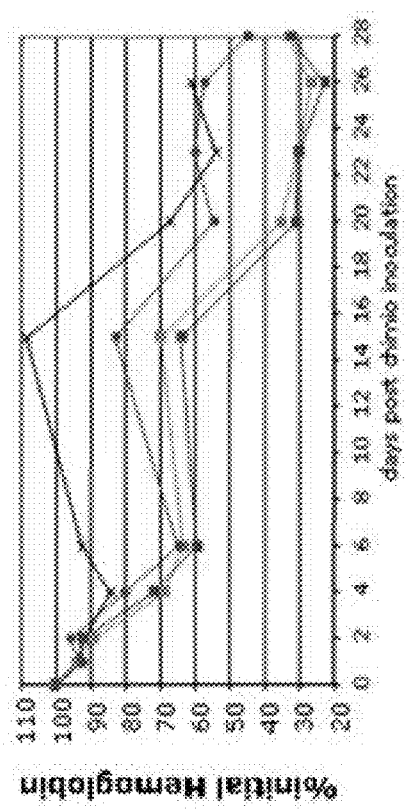
Figure 10:
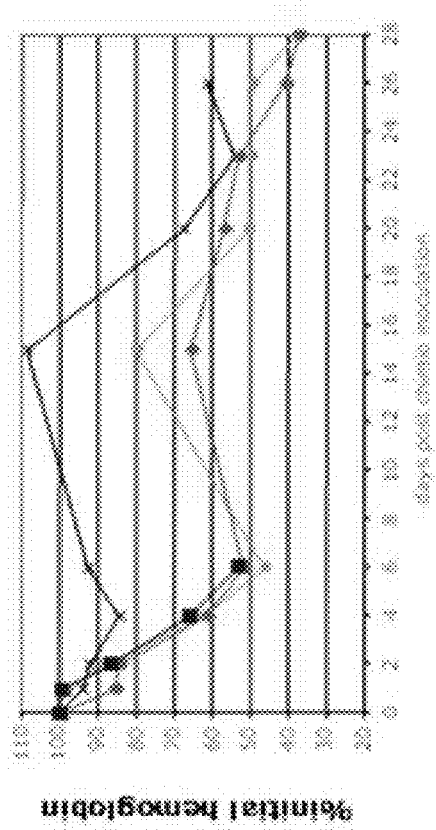
FIG. 10 illustrates a graph of the effect of oxaliplatin on bone marrow products in animals implanted with tumor and controls in accordance with an embodiment of the present disclosure.
Figure 10:
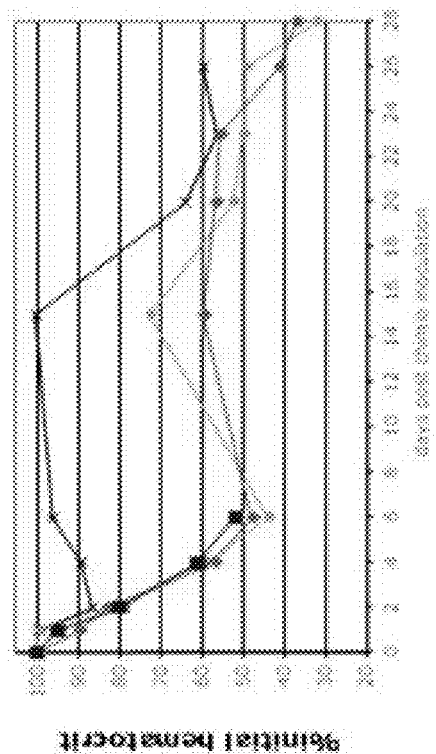

Our data shows that cancer therapy creates an initial insult to the bone marrow, and therefore also to the blood and immune cell production. This insult, or toxicity, from the cancer therapy begins immediately after the administration of a chemotherapeutic agent and continues for several days. Our data shows that the tumor itself also suppresses bone marrow activity as demonstrated by the low blood cells counts. The figures (FIGS. 9 & 10) demonstrate how toxicity has a rapid onset with a decline that continues for approximately one week. However, one week following administration of the cancer therapy, the body begins to recover, as evident by the improvements in blood cell measures. At this time the growth rate of the tumor has been suppressed, but the tumor is still viable. The second phase of bone marrow toxicity caused by the tumor occurs and a decline is once again observed in the blood cell measures.

Traditional cancer therapy includes multiple administrations of chemo-, radio- and/or immunotherapy. The neoadjuvant strategy is to use fewer doses of chemo- or radiotherapy in an effort to reduce the growth rate or size of the tumor prior to the major intervention (e.g., surgery or more aggressive chemotherapy regimens). However, oncologists will delay these major interventions if the patient's blood cell (e.g. hematocrit, platelet, immune cell) counts are too low which places the individual at increased risk for infection, bleeding, and even respiratory difficulties. A solution to these problems is sought and addressed by the novel intervention strategies described herein.

Our data illustrates the toxicity in two-phases. First, toxicity caused by the cancer therapy. Second, toxicity induced by the tumor itself. Therefore, it is proposed to use a two-phase approach to treating and/or preventing bone marrow toxicity caused by the cancer therapy and the tumor.

Nutritional interventions that include combinations of compounds with immune-cell stimulating activity are expected to benefit the individual by 1) preventing the severe bone marrow toxicity in the first phase and 2) increasing the immunologic response during the tumor-induced toxic phase.

Example

Figure 11:
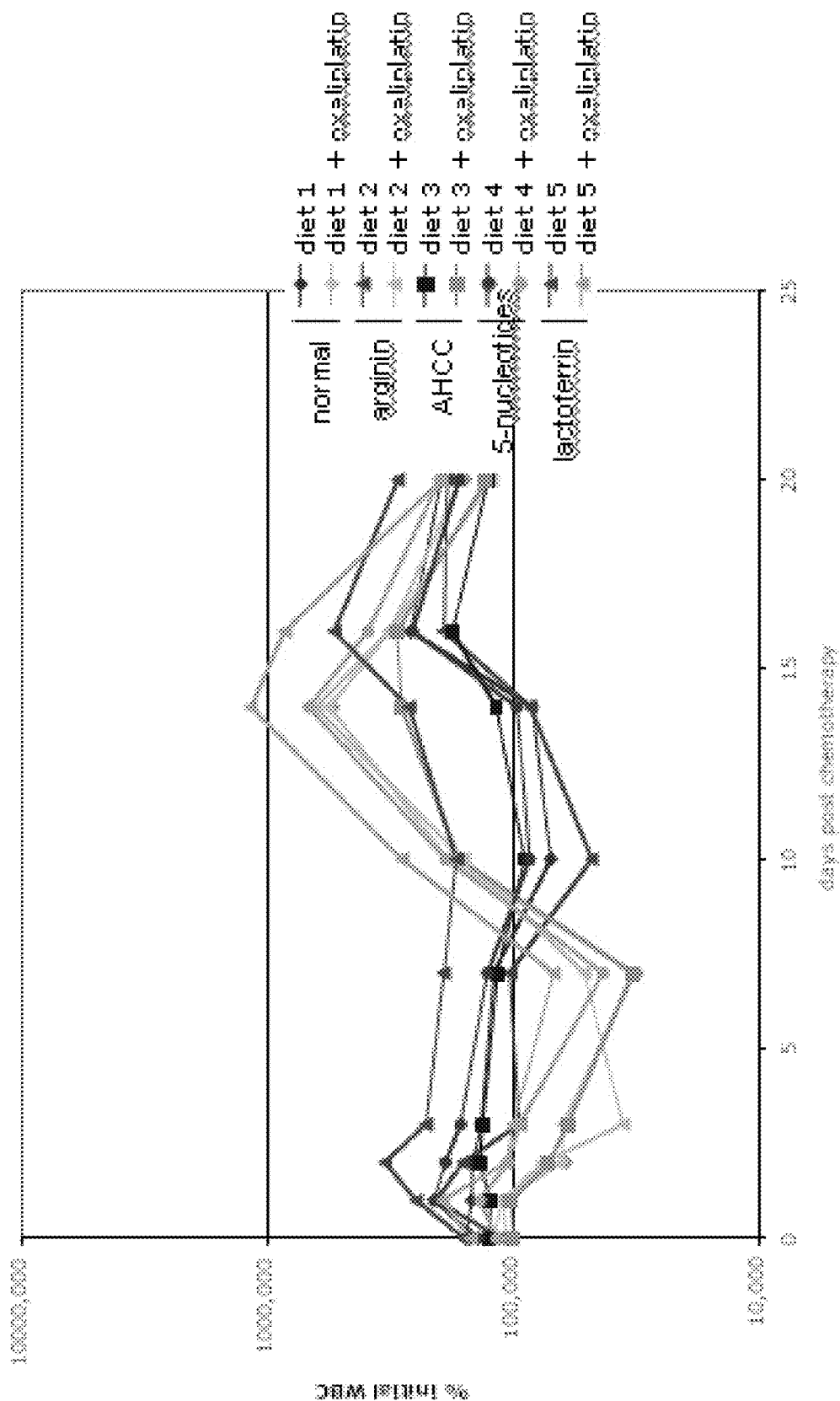
FIG. 11 illustrates a graph of the effect of nutritional intervention on immune cells in tumor burdened animals with and without chemotherapy in accordance with an embodiment of the present disclosure.

According to our data, and in alignment with the previously described hypothesis, administration of Lactoferrin (compound 5) resulted in the less toxicity in the chemotherapy treated group (FIG. 11) as compared to the control.

The Lactoferrin-treated group experienced an increase in their immune cell population during the second phase. In addition, there was an increase immune cell concentration reported for both dietary nucleotides (Diet 4) as well as arginine (Diet 2) during the second phase. Therefore, oral administration of a combination including these compounds is believed to reduce the bone marrow suppression associated with both phases of the two-phase toxicity. The evidence supports our hypothesis that administration of specific nutritional compounds can reduce bone marrow toxicity which can improve the patient's adherence to the cancer treatment protocol, quality of life, and reduced risk of comorbidities.

Neo-Adjuvant Therapy

The following invention examples are based on the use of nutritional support of cancer therapy that may include, but is not limited to, neo-adjuvant cancer therapy. Neoadjuvant therapy is an emerging method of treating digestive cancers such as esophageal and rectal tumors, as well as head and neck cancers and other cancers. Neoadjuvant therapy is pre-treatment with either radiotherapy, chemotherapy, hormone therapy, or combinations of these in advance of the main therapy where main therapy is surgery or more aggressive chemo- or radiotherapy. The rationale for such pre-treatment before the main treatment is to improve therapeutic possibilities. The proposed benefits of neoadjuvant cancer therapy, as well as the nutritional support include, but are not limited to: reduced tumor size, better chance of complete tumor resection (surgical intervention), risk reduction of tumor seeding during operation, prevention of local or systemic recurrences, and a better overall patient outcome. In addition, it is believed this approach will diminish acute and chronic treatment toxicities, operative and perioperative morbidity, and improve the patient's quality of life.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A method of attenuating chemotherapy-induced neutropenia, the method comprising:
    administering enterally an immunonutritional composition to a subject having chemotherapy-induced neutropenia, the subject is undergoing an anti-cancer therapy that comprises an aggressive treatment selected from the group consisting of surgery that removes all or part of a tumor, hormonal treatment that induces apoptosis, radiotherapeutic treatment that induces apoptosis, chemotherapeutic treatment that induces apoptosis, and combinations thereof, and the anti-cancer therapy further comprises neoadjuvant chemotherapeutic treatment before the aggressive treatment, and the composition is administered daily to the subject for a time period extending from a first date between ten and three days before the neoadjuvant chemotherapeutic treatment to a second date between ten and seven days after the aggressive treatment,
    wherein the composition comprises immuno-enhancing agents comprising L-arginine, omega-3 fatty acids, and nucleotides.

2. The method of claim 1, wherein the aggressive treatment is surgery that removes all or part of a tumor.

3. The method of claim 1, wherein the aggressive treatment is hormonal treatment that induces apoptosis.

4. The method of claim 1, wherein the aggressive treatment is radiotherapeutic treatment that induces apoptosis.

5. The method of claim 1, wherein the aggressive treatment is chemotherapeutic treatment that induces apoptosis.

6. The method of claim 1, wherein the immunonutritional composition is a tube feed.

7. The method of claim 1, wherein the immunonutritional composition is gel.

8. The method of claim 1, wherein the immunonutritional composition is a complete nutritional.

9. The method of claim 1, wherein the composition comprises an additional immunoenhancing agent selected from the group consisting of a probiotic, a probiotic biomass, non-replicating organisms, potassium, uric acid, a single-stranded oligonucleotide, a pathogen/microbial associated molecular pattern (PAMP/MAMP), an active hexose correlated compound, carotenoids, a vitamin D receptor, branched-chain amino acids, theanine, vitamin E, lactoferrin protein, and combinations thereof.

10. The method of claim 1, wherein the composition comprises a protein source selected from the group consisting of whey protein; casein protein; soy protein; hydrolysates of whey, casein, or soy protein; and combinations thereof.

* * * * *